US012616615B2

(12) United States Patent
Al Aioubi et al.

(10) Patent No.: US 12,616,615 B2
(45) Date of Patent: May 5, 2026

(54) SENSING DEVICE FOR A NAPPY

(71) Applicant: Oxford Healthtech Ltd., Newbury (GB)

(72) Inventors: Mohamad Yasser Al Aioubi, Didcot (GB); Syed Ejazul Huq, Abingdon (GB)

(73) Assignee: Oxford Healthtech Ltd., Newbury (GB)

( * ) Notice: Subject to any disclaimer, the term of this patent is extended or adjusted under 35 U.S.C. 154(b) by 403 days.

(21) Appl. No.: 18/554,370

(22) PCT Filed: Apr. 6, 2022

(86) PCT No.: PCT/GB2022/050862
§ 371 (c)(1),
(2) Date: Oct. 6, 2023

(87) PCT Pub. No.: WO2022/214807
PCT Pub. Date: Oct. 13, 2022

(65) Prior Publication Data
US 2024/0238130 A1     Jul. 18, 2024

(30) Foreign Application Priority Data

Apr. 8, 2021     (GB) ...................................... 2105043

(51) Int. Cl.
*A61F 13/42*          (2006.01)
*A61F 13/49*          (2006.01)
(52) U.S. Cl.
CPC .............. *A61F 13/42* (2013.01); *A61F 13/49* (2013.01); *A61F 2013/423* (2013.01); *A61F 2013/424* (2013.01)
(58) Field of Classification Search
CPC ................ A61F 13/42; A61F 2013/423; A61F 2013/424
See application file for complete search history.

(56) References Cited

U.S. PATENT DOCUMENTS

| | | | |
|---|---|---|---|
| 9,138,354 B2 * | 9/2015 | Nhan | ................ A61F 13/00055 |
| 10,350,115 B2 * | 7/2019 | Long | ...................... A61F 13/42 |

(Continued)

FOREIGN PATENT DOCUMENTS

| | | |
|---|---|---|
| GB | 2596183 A | 12/2021 |
| KR | 20200136328 A | 12/2020 |
| WO | WO 2021/069899 A1 | 4/2021 |

OTHER PUBLICATIONS

International Preliminary Report on Patentability received in corresponding Application No. PCT/GB2022/050862, dated Oct. 10, 2023, 6 pages.

(Continued)

*Primary Examiner* — Catharine L Anderson
(74) *Attorney, Agent, or Firm* — Dority & Manning, P.A.

(57)          ABSTRACT

There is described a sensing device for attaching to an external surface of a nappy. The sensing device comprises an expandable member comprising one or more elastic elements extending between a plurality of attachment points, wherein the attachment points are configured to fixedly attach the expandable member to the external surface of the nappy, and wherein the one or more elastic elements are configured to stretch as the attachment points move apart such that the expandable member is configured to expand in accordance with expansion of the nappy. The sensing device further comprises a detector unit coupled to the expandable member, wherein the detector unit is configured to detect expansion of the expandable member, and is further configured to determine a nappy fullness parameter based on the detected expansion of the expandable member.

20 Claims, 21 Drawing Sheets

(56)          References Cited

U.S. PATENT DOCUMENTS

| | | |
|---|---|---|
| 2007/0252714 A1 | 11/2007 | Rondoni et al. |
| 2010/0164733 A1 | 7/2010 | Ales et al. |
| 2013/0165809 A1* | 6/2013 | Abir ........................ A61B 5/113 |
| | | 600/534 |

OTHER PUBLICATIONS

International Search Report received in corresponding Application No. PCT/GB2022/050862, dated Jul. 14, 2022, 3 pages.
Search Report received in corresponding Application No. GB 2105043.0, dated Sep. 17, 2021, 4 pages.
Written Opinion received in corresponding Application No. PCT/GB2022/050862, dated Jul. 14, 2022, 4 pages.

* cited by examiner

SENSING DEVICE FOR A NAPPY

CROSS-REFERENCE TO RELATED APPLICATIONS

This application is a U.S. national phase application of International Patent Application No. PCT/GB2022/050862, filed on Apr. 6, 2022, which, in turn, is based upon and claims the right of priority to European Patent Application No. 2105043.0, filed on Apr. 8, 2021, the disclosures of all of which are hereby incorporated by reference herein in their entireties by reference for all purposes.

FIELD OF INVENTION

This invention relates to a sensing device for attaching to an external surface of a nappy so as to determine a nappy fullness parameter. This invention also relates to a combined nappy and sensing device. Sensing elements of the sensing device can be attachable to or integrated onto the external surface of the nappy.

BACKGROUND

Incontinence products such as nappies/diapers, incontinence pads and underwear allow a wearer to urinate and/or defecate without using a lavatory. The incontinence products comprise an absorbing layer to contain urine and/or feces and prevent leakage onto outer clothing. Incontinence products can be used for children (bed wetting) as well adults, particularly those with illnesses linked to incontinence. When a nappy, or other incontinence product, becomes soiled with urine and/or feces, it requires changing, usually by another person (e.g., a carer). Since nappy wearers may be often unable to replace the nappy themselves, or even be unable to communicate that the nappy requires changing, the carer must manually check the nappy for soiling periodically throughout the day. This involves changing the nappy, possibly unnecessarily, thereby wasting the carer's valuable time and associated costs. On the other hand, failure to change a nappy on a sufficiently regular basis may lead to problems such as the wearer feeling uncomfortable, a negative effect on the wearer's dignity, and/or skin problems, such as rashes, bed sores, and infections. Therefore, there is a need for an improved process for detecting the fullness of a nappy, or other incontinence products. Detecting fullness of a nappy would also be useful for babies.

SUMMARY

According to a first aspect of the present invention, there is provided a sensing device for attaching to an external surface of a nappy. The sensing device comprises an expandable member. The expandable member comprises one or more elastic elements extending between a plurality of attachment points. The attachment points are configured to fixedly attach the expandable member to the external surface of the nappy. Preferably, some or all of the attachment points are disposed on or near to edges of the nappy, such as elasticated edges. The one or more elastic elements are configured to stretch as the attachment points move apart such that the expandable member is configured to expand in accordance with expansion of the nappy (i.e. as the nappy fills up). The sensing device further comprises a detector unit coupled to the expandable member. The detector unit is configured to detect expansion of the expandable member. The detector unit is further configured to determine a nappy fullness parameter based on the detected expansion of the expandable member. According to a second aspect of the present invention, there is provided a combined nappy and sensing device comprising a nappy and the sensing device described above. The sensing device further comprises an electronic control and power supply unit configured to power the sensing device. The electronic control and power supply unit preferably includes the detector unit described above. The attachment points of the expandable member are fixedly attached to the external surface of the nappy.

In some examples, the sensing device is attached to the external surface of the nappy after the nappy has been manufactured. In other examples, the expandable member of the sensing device is integrated onto (i.e., created on) the external surface of the nappy during manufacture. The detector unit may then be attached to the expandable member, e.g., via a loop.

There are also other advantageous aspects of the invention described in the detailed description below.

BRIEF DESCRIPTION OF THE DRAWINGS

In order that the invention can be more readily understood, reference will now be made by way of example only, to the accompanying drawings in which:

In FIG. 9$a$, an expandable member of the sensing device is in an unexpanded state.

FIG. 9$b$ is a plan view of the arrangement of FIG. 9$a$.

FIG. 9$c$ is a cross-sectional view of the exemplary optical detector in FIGS. 9$a$-9$b$, when the expandable member of the sensing device is in an expanded state. FIG. 9$d$ is a plan view of the arrangement of FIG. 9$c$.

In FIG. 11$a$, the expandable member of the sensing device is in an unexpanded state.

FIG. 11$b$ is a cross-sectional view of the exemplary optical detector in FIG. 11$a$, when the expandable member of the sensing device is in an expanded state.

DETAILED DESCRIPTION

Figure 1:
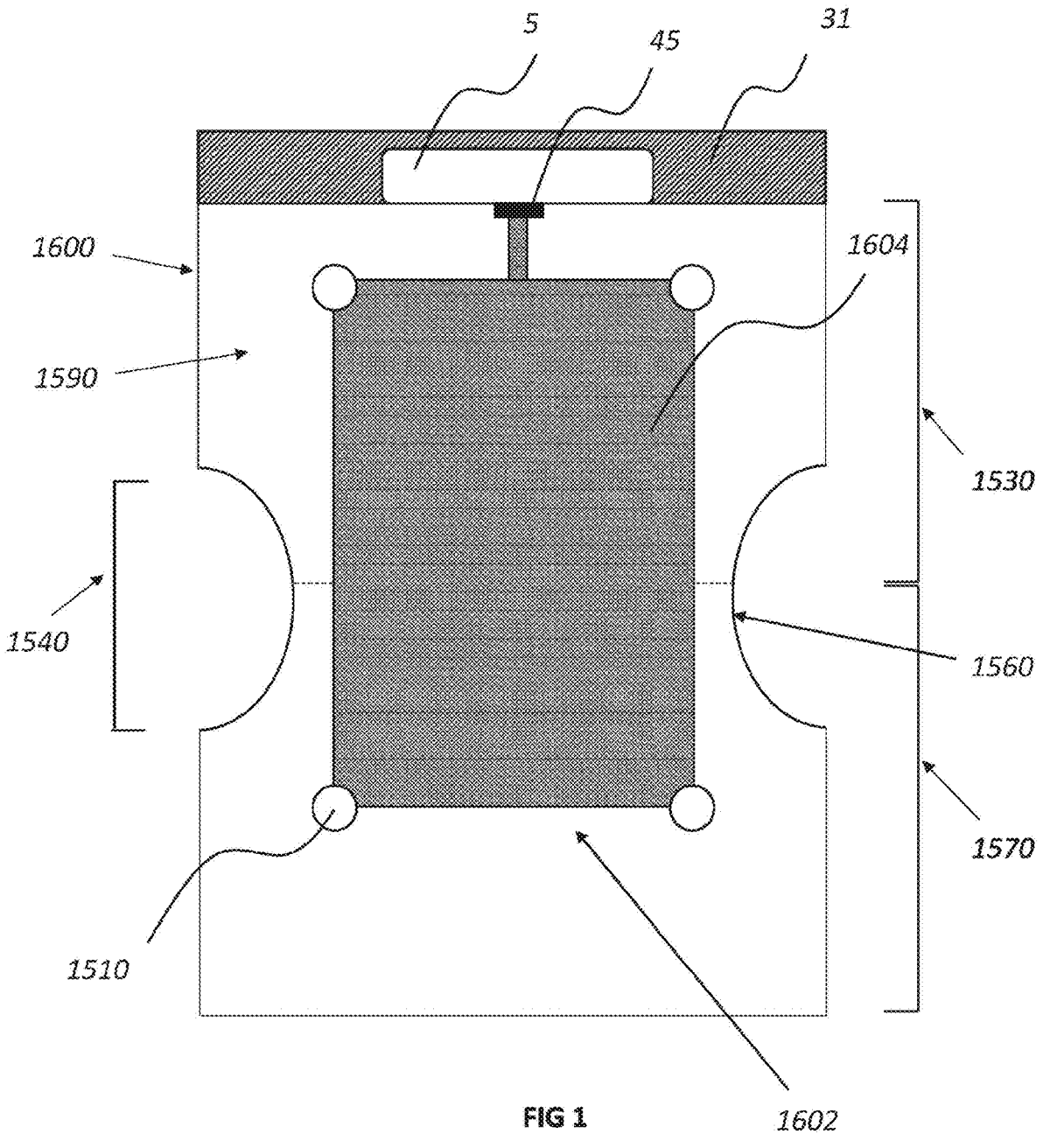
FIG. 1 is a plan view of an exemplary sensing device attached to the external surface of a nappy.

There are described herein sensing devices suitable for attaching to an external surface of a nappy. Each sensing device comprises an expandable member. The expandable member comprises one or more elastic elements extending between a plurality of attachment points. The attachment points are configured to fixedly attach the expandable member to the external surface of the nappy. Preferably, some or all of the attachment points are disposed on or near to edges of the nappy, such as elasticated edges. The one or more elastic elements are configured to stretch as the attachment points move apart such that the expandable member is configured to expand in accordance with (volume) expansion of the nappy. The sensing device further comprises a detector unit coupled to the expandable member. The detector unit is configured to detect expansion of the expandable member. The detector unit is further configured to determine a nappy fullness parameter based on the detected expansion of the expandable member. The detector unit may comprise a gyroscope or an accelerometer configured to detect movement. For example, the gyroscope or accelerometer may detect movement of the nappy wearer during nappy use.

There is also herein described a combined nappy and sensing device comprising a nappy and the sensing device described above. The sensing device further comprises an electronic control and power supply unit configured to power the sensing device. The electronic control and power supply unit preferably includes the detector unit described above. The attachment points of the expandable member are fixedly attached to the external surface of the nappy. In some examples, the sensing device is attached to the external surface of the nappy after the nappy has been manufactured. In other examples, the expandable member of the sensing device is integrated onto (i.e., created on) the external surface of the nappy during manufacture. The detector unit may then be attached to the expandable member, e.g., via a loop.

A nappy may also be referred to as a diaper analogously herein. The nappy may be sized to be worn by an adult person, a child or a baby, and may be of any suitable design and absorbency. As mentioned above, the sensing device may be produced separately from the nappy, and so can be applied to any type of nappy, or other incontinence product. The sensing device is attached to the external surface of the nappy after the nappy has been manufactured. Alternatively, the expandable member of the sensing device may be integrated onto (i.e., created on) the external surface of the nappy during the nappy manufacturing process, and the detector unit attached at a later point. These are in contrast to prior nappy wetness/fullness sensing technologies, where active sensing elements (e.g., electrical and chemical elements) have been produced separately and integrated into the inside of the nappy, and the active sensing elements are in physical contact with the urine absorbency layer of the nappy, which is complicated and costly.

An example of a sensing device attached to a nappy is shown in FIG. 1. FIG. 1 shows a plan view nappy 1600, with an external surface 1590, before it is worn. The nappy 1600 includes a front 1530 connected to a waistband section 31. The front 1530 of the nappy 1600 is connected to a back 1570 of the nappy 1600 by a crotch region 1540. When the nappy 1600 is worn, the front 1530 of the nappy 1600 is positioned against the wearer's pubic region and lower abdomen, the back 1570 of the nappy 1600 is positioned against the wearer's bottom, and the crotch region 1540 of the nappy 1600 is positioned over the wearer's groin and between their legs.

The nappy 1600 has elasticated edges 1560 that extend around the top of the wearer's legs. The elasticated edges 1560 are stretchable so as to allow the nappy to be worn comfortably, and follow the contours of the wearer's body to stop the leakage of fluids from the nappy 1600. The external surface 1590 of the nappy 1600 is usually made of a non-stretch material. In this case, the nappy 1600 is nonetheless able to expand because of the elasticated edges 1560, and because the external surface 1590 is configured to be relatively loose when a wearer first puts on the nappy 1600 (i.e. when the nappy contains no feces/urine). In addition, creasing of the nappy material (as described below) aids expansion.

FIG. 1 also shows a sensing device attached to the nappy 1600. The sensing device comprises an expandable member 1602 coupled to a detector unit 5. The expandable member 1602 comprises an elastic element 1604 extending between a plurality of attachment points 45, 1510. The attachment points are configured to fixedly attach the expandable member 1602 to the external surface of the nappy 1600.

Figure 22:
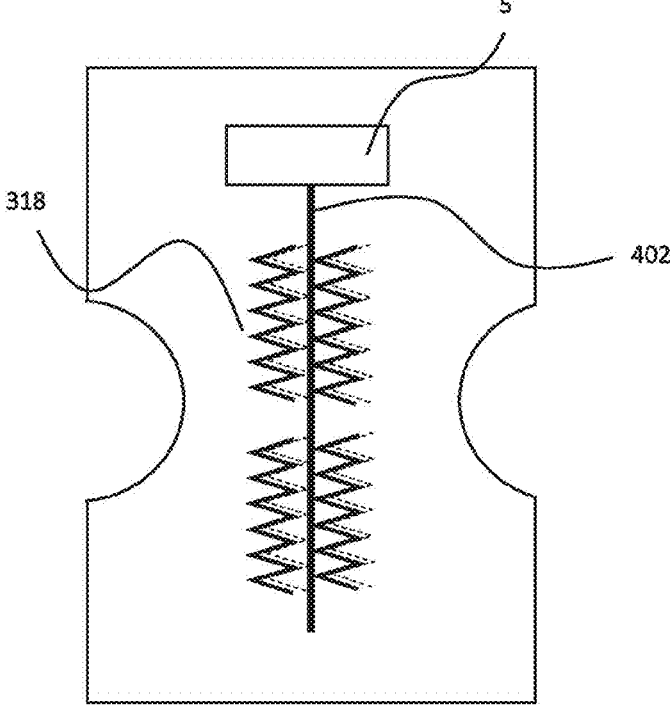
FIG. 22 a plan view of an exemplary integrated sensor configuration of the sensing device on the external surface of a nappy.

The sensing device may be attached to the nappy via the attachment points after the nappy has been manufactured, and in this case is both detachable and reusable. Alternatively, the expandable member may be integrated onto (i.e., created on) the external surface of the nappy during manufacture. In this case, the expandable member is created on the external top surface material of the nappy, as an integral part of the nappy, during the nappy manufacturing process. This may be achieved in different ways. For example, it is well known that some nappies comprise a top layer of non-stretch material placed on top of, and glued to, a stretchable polymeric (e.g., rubber-like) under material. In the nappy manufacturing process, the two layers can be creased up in selected areas to create an elastic, wearable nappy. E.g., the creased areas of the nappy stretch when worn. If the nappy does not comprise a stretchable under layer, then the composition of the top surface material can be changed to make it elastic (the whole of the top material may be made elastic or only selected areas). During the nappy manufacturing process, the expandable member may be created (e.g., integrated) on the external surface of the nappy in these creased areas. Preferably the creased areas are created in the direction of the manufacturing process. FIG. 22 shows an example of an integrated sensor configuration. A central element 402 experiences a pull when creased areas 318 stretch, as the nappy fills up. The solid zigzag lines represent the top layer of non-stretch material. The dashed zigzag lines represent the stretchable polymeric under material. The central element 402 may be integrated onto (i.e., created on) the external surface of the nappy. The pull on the central element 402 exerts a pulling force on the detector unit 5 resulting in a change in a detected signal produced in the detector unit 5. This expansion measurement is described in further detail below.

When the external surface of the nappy 1600 is made of a non-stretch material (as is generally the case), it is important that at least some of the attachment points are positioned on, or close to, edges (e.g. the elasticated edges 1560) of the nappy 1600, so as to capture the nappy expansion. In this regard, FIG. 1 is merely a schematic representation, and it will be understood that the corner attachment points 1510 may actually be disposed very close to the lateral (elasticated) edges 1560 of the nappy. Alternatively, there may be additional attachment points connecting the elastic element 1604 to the elasticated edges 1560 of the nappy 1600. However, if the expandable member is created on the external surface of the nappy during the manufacturing process, then it is not always necessary to position the attachment points on, or close to, edges of the nappy. This is because the creased areas of the nappy will naturally expand as the nappy volume increases (e.g., as the nappy fills with urine and/or feces). As such, it not necessary to take advantage of the elasticated edges of the nappy. The detector unit 5 is mounted on the waistband 31 of the nappy 1600. Alternatively, the detector unit 5 may be mounted on any other suitable part of the external surface 1590 of the nappy 1600, such as the front 1530 of the nappy 1600, near the waistband 31. The detector unit 5 is coupled to the expandable member 1602. For example, in FIG. 1, the attachment points comprise a detector unit attachment point 45 directly coupled to the detector unit 5. The detector unit attachment point 45 is positioned centrally on the front 1530 of the nappy 1600 just below, or on, the waistband section 31 of the nappy 1600. The detector unit 5 is configured to detect expansion of the expandable member 1602 as the nappy 1600 expands. The detector unit 5 may comprise an optical detector, a resistive detector, a capacitive detector, or any other detector suitable for sensing expansion of the expandable member 1602. There may also be additional electronics for data storage and communication inside the detector unit 5, such as a gyroscope or an accelerometer configured to detect movement detect movement of the nappy wearer during nappy use.

The elastic element 1604 of the expandable member 1602 is an elastic patch in FIG. 1. The attachment points include attachment points 1510 at corners of the elastic patch. Thus, the expandable member 1602 of FIG. 1 includes only one elastic element 1604 in the form of a rectangular elastic patch extending between the plurality of attachment points 45, 1510, and positioned centrally across a substantial area of the front 1530, the crotch region 1540, and the back 1570 of the nappy 1600. Two of the attachment points 1510 are positioned on the front 1530 of the nappy 1600, at the first two corners of the elastic patch, which are equidistant from the waistband 31. Two more of the attachment points 1510 are positioned on the back 1570 of the nappy 1600, at the remaining two corners of the elastic patch. There may be additional attachments points connecting the elastic patch 1604 to the elasticated edges 1560 of the nappy. The elastic patch can expand in accordance with the volume expansion of the nappy 1600 when there is urine and/or feces ingress inside the nappy 1600. In FIG. 1, the elastic patch is rectangular. However, the elastic patch may be any suitable shape, such as a square, circle or oval. The attachments points 1510 may be positioned at the corners, or around the edges/periphery, of the elastic patch.

The expandable member 1602 is sized and shaped to cover a substantial area of the external surface 1590 of the nappy 1600 in FIG. 1. In some examples, the expandable member may cover a substantial part of each of the front of the nappy, the back of the nappy, the crotch region of the nappy, the elasticated edges of the nappy, or a combination thereof. For example, in FIG. 1, the expandable member 1602 covers a substantial part of the front 1530 of the nappy 1600, a substantial part of the crotch region 1540 of the nappy 1600 and a substantial part of the back 1570 of the nappy 1600. In other examples, the expandable member 1602 may be sized and shaped to extend across a full width of the crotch region 1540 of the nappy 1600 (see FIG. 7 for one example).

The attachment points 45, 1510 are configured to fixedly attach the expandable member 1602 to the external surface 1590 of the nappy 1600. For example, the attachments points 45, 1510 are fixedly attached using an attachment mechanism, such as glue, adhesive, ultrasound bonding, hook-and-loop pads, poppers, magnets, stitching, riveting, welding, or any other suitable attachment mechanism. As mentioned above, the fixing may occur during or after manufacture of the nappy. The attachment points 45, 1510 of the expandable member 1602 may be fixedly attached to the front 1530 of the nappy 1600, the back 1570 of the nappy 1600, the crotch region 1540 of the nappy 1600, the elasticated edges 1560 of the nappy 1600, or a combination thereof.

As the nappy 1600 expands, the attachment points 45, 1510 move further apart which creates a pulling force on the detector unit attachment point 45 away from the detector unit 5, as will be discussed in more detail later on. The elastic element 1604 is configured to stretch as the attachment points 45, 1510 move apart such that the elastic element 1604 expands in accordance with expansion of the nappy 1600. In other words, the elastic element 1604 is free to change in length and width in accordance with expansion of the nappy 1600 as the nappy 1600 fills with urine and/or feces. To facilitate stretching, the elastic element 1604 may be made of an elastomer material. For example, an elastomer material having a low Young's modulus and high failure strain. The material property of the elastomer is chosen such that it functions in accordance with the nappy material. For example, the elastomer material closely follows the expansion properties of the nappy material, particularly at the elasticated edges 1560 of the nappy 1600. The elastic element 1604 may be made from a conducting or non-conducting polymer. A conducting elastomeric material is particularly useful if the sensing device is configured to detect a change in resistance or capacitance as the material expands along with the nappy 1600 when there is urine and/or feces ingress inside the nappy 1600 (see the examples described below in connection with FIGS. 16 and 17).

In use, the sensing device is configured to determine a nappy fullness parameter based on the detected expansion of the expandable member 1602. As the nappy 1600 fills with urine and/or feces it begins to expand. As the nappy 1600 expands, the attachment points 45, 1510 are moved apart from each other, producing a relative displacement between the attachment points 45, 1510. In turn, this causes the elastic element 1604 to stretch. The detector unit 5 is configured to detect expansion of the expandable member 1602 by (indirectly) detecting the relative displacement between the attachment points 45, 1510. For example, as the nappy 1600 expands and the attachment points 45, 1510 are moved apart from each other, a relative displacement between the attachment points 45, 1510 is produced. As the elastic element 1604 stretches, it exerts a pulling force on the detector unit 5, via the detector unit attachment point 45, resulting in a change in a detected signal produced in the detector unit 5. In other words, the detector unit 5 detects a pull on the detector unit 5 caused by expansion of the nappy 1600. The change in the detected signal is proportional to the overall volume expansion of the nappy 1600, due to the ingress of urine and/or feces inside it. As described in more detail below with reference to FIGS. 9-17, the detector unit 5 generates an output signal, either an analogue or a digital electrical signal, that is representative of the displacement and therefore nappy expansion. The detected expansion of the expandable member 1602 is proportional to the overall nappy expansion as urine and/or feces ingress the nappy 1600. Thus, the detector unit 5 is indirectly responsive to changes in displacement between the attachment points 45, 1510 on the external surface 1590 of the nappy 1600. This is contrast to prior approaches, where the nappy fullness is determined using a moisture sensor inside the nappy to sense moisture/wetness of the nappy, or using a pressure sensor to sense increased radial pressure between the wearer and the nappy. The detector unit 5 may detect the displacement using any displacement or strain detector technology, but preferred examples, as described below, include an optical detector, a capacitive detector, and/or a resistive detector.

Figure 2:
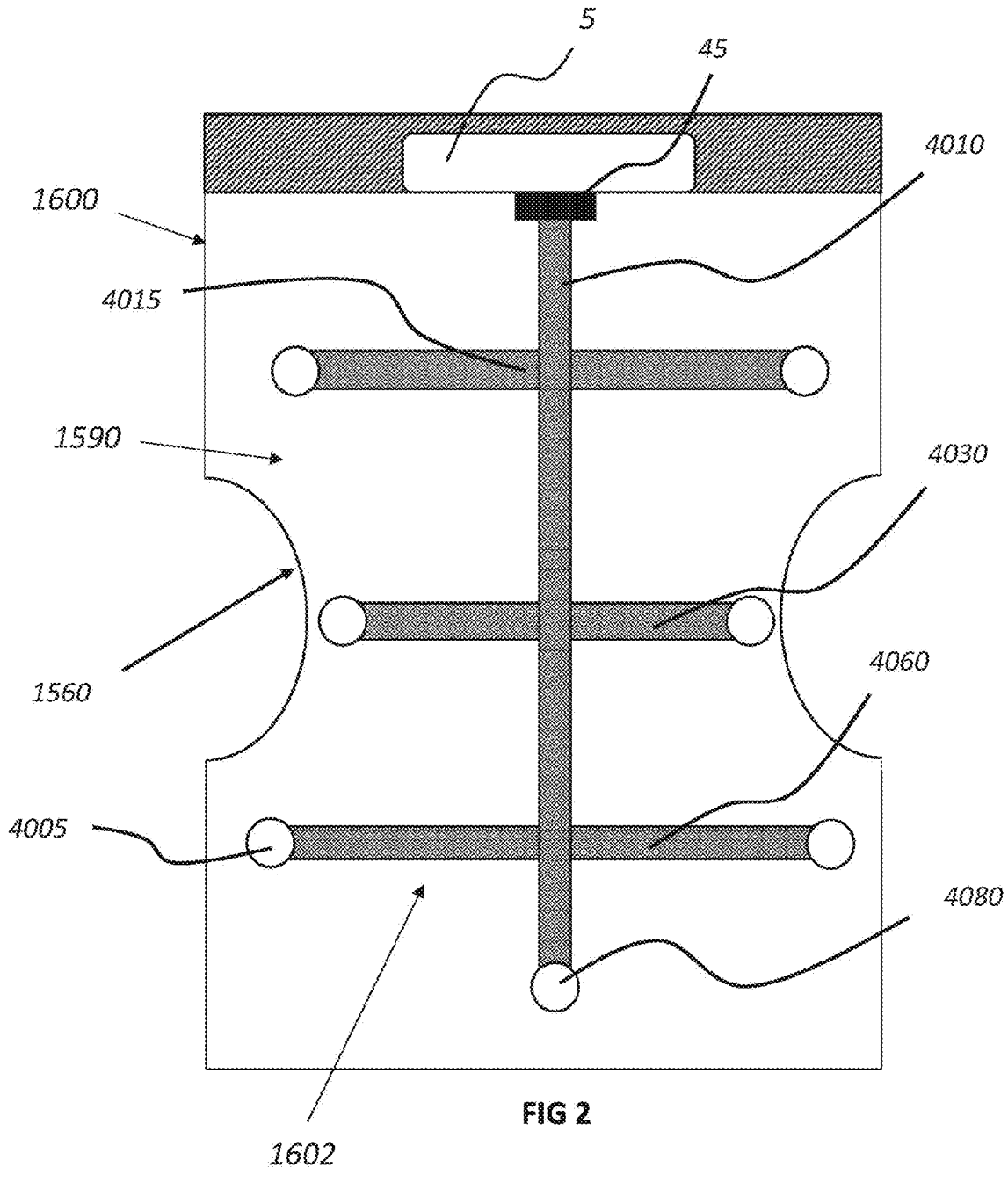
FIGS. 2-8 are plan views of alternative configurations of exemplary sensing devices attached to the external surface of a nappy.

FIG. 2 shows an alternative configuration of an expandable member 1602 of a sensing device attached to the external surface 1590 of a nappy 1600. In this configuration, the attachment points comprise a first attachment point 4080 connected to a detector unit attachment point 45 via a longitudinal elastic element 4010. For example, the detector unit attachment point 45 is positioned next to the detector unit 5, as in FIG. 1. The first attachment point 4080 is positioned centrally on the back 1570 of the nappy 1600. The longitudinal elastic element 4010 may be a central elasticated strip or thread attached to the nappy 1600 at the first attachment point 4080 and the detector unit attachment point 45. The remaining length of the longitudinal elastic element 4010 is free to expand. The attachment points also comprise one or more secondary attachment points 4005 connected to the longitudinal elastic element 4010 via one or more transverse elastic elements 4015, 4030, 4060. The secondary attachment points 4005 are located close to the lateral (elasticated) edges 1560 of the nappy 1600. In FIG. 2, the transverse elastic elements 4015, 4030, 4060 are positioned such that there is one 4015 on the front 1530 of the nappy, one 4030 on the crotch region 1540 of the nappy 1600, and one 4060 on the back 1570 of the nappy 1600. The transverse elastic elements 4015, 4030, 4060 extend towards the elasticated edges 1560 of the nappy 1600, so as to capture the nappy expansion at the elasticated edges 1560 of the nappy 1600. The transverse elastic elements 4015, 4030, 4060 may also be elasticated strips or threads, and are free to expand between the attachment points 4005 at their ends. As the nappy expands, the transverse elastic elements 4015, 4030, 4060 exert additional force on the longitudinal elastic element 4010, and thereby on the detector unit 5. Advantageously, these transverse elastic elements 4015, 4030, 4060 allow more accurate measurement of the expansion of the nappy 1600 because there is more coverage of the external surface 1590 of the nappy 1600 by the expandable member 1602. The elastic elements 4010, 4015, 4030, 4060 extend in two different directions (horizontally and vertically in FIG. 2). Therefore, it is possible to more accurately detect the relative displacement of the attachment points 45, 4080, 4005, thus producing a more accurate determination of the volume expansion of the nappy 1600. In one example, the transverse elastic element 4030 may extend fully to the elasticated edges 1560 of the nappy 1600. In this case, expansion of the transverse elastic element 4030 will follow expansion of the elasticated edges 1560, thereby helping account for movement of the wearer's body. FIG. 2 relates to examples where the sensing device is attached to the external surface of the nappy after the nappy has been manufactured, and examples where the expandable member of the sensing device is integrated onto the external surface of the nappy during manufacture.

Figure 3:
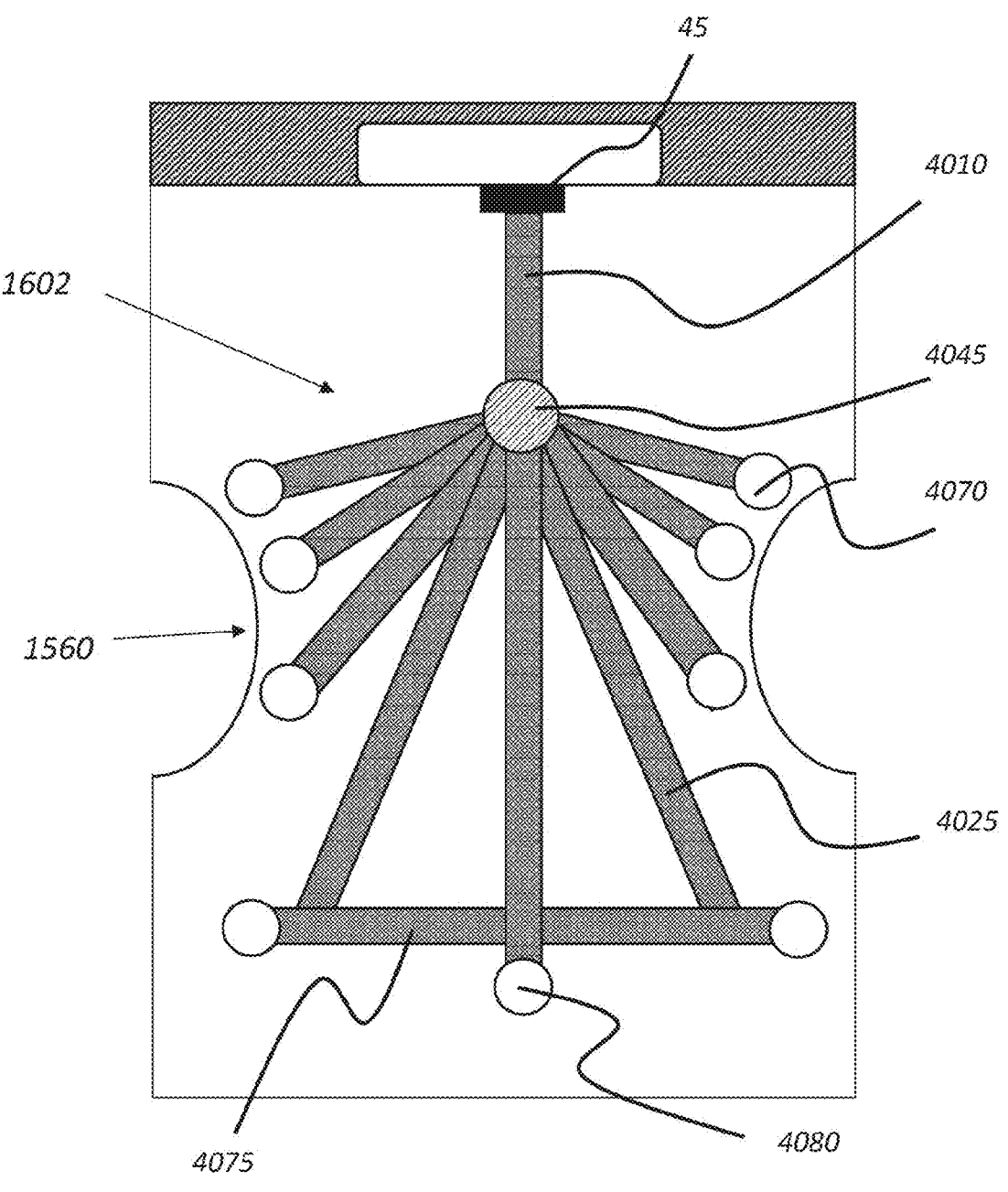

FIG. 3 shows an alternative configuration of an expandable member 1602 of a sensing device. In this configuration, there is a central junction point 4045 connected to the detector unit attachment point 45 via a central elastic element 4010. The central junction point 4045 (shown by a hashed circle in FIG. 3) is not fixedly attached to the external surface 1590 of the nappy 1600, and is therefore free to move as the nappy 1600 expands. In FIG. 3, the central junction point 4045 is positioned centrally over the front 1530 of the nappy 1600, and the central elastic element 4010 extends centrally across the front 1530 of the nappy 1600 between the central junction point 4045 and the detector unit attachment point 45. The attachment points also comprise multiple attachment points 4070, 4080 spaced around the central junction point 4045, the multiple attachment points 4070, 4080 connected to the central junction point 4045 via respective radial elastic elements 4025. In FIG. 3, the multiple attachment points 4070, 4080 are positioned predominately in the crotch region 1540 of the nappy 1600, near to the elasticated edges 1560 of the nappy 1600. In addition, some of the multiple attachment points 4070, 4080 are positioned on the back 1570 of the nappy 1600, near to the elasticated edges 1560 of the nappy 1600. The spacing of the attachment points 4070, 4080 aids in expansion detection, as each radial elastic element 4025 adds to the force experienced by the central elastic element 4010, and therefore by the detector unit 5. The elastic elements 4010, 4025 are free to expand between the attachment points 45, 4080, 4070. The expandable member 1602 may also include further elastic elements connected between the multiple attachment points 4070, 4080. For example, in FIG. 3, a further transverse elastic element 4075 is connected between attachment points 4070 on the back 1570 of the nappy 1600, near to the elasticated edges 1560 of the nappy 1600. FIG. 3 relates to examples where the sensing device is attached to the external surface of the nappy after the nappy has been manufactured, and examples where the expandable member of the sensing device is integrated onto the external surface of the nappy during manufacture.

Figure 4:
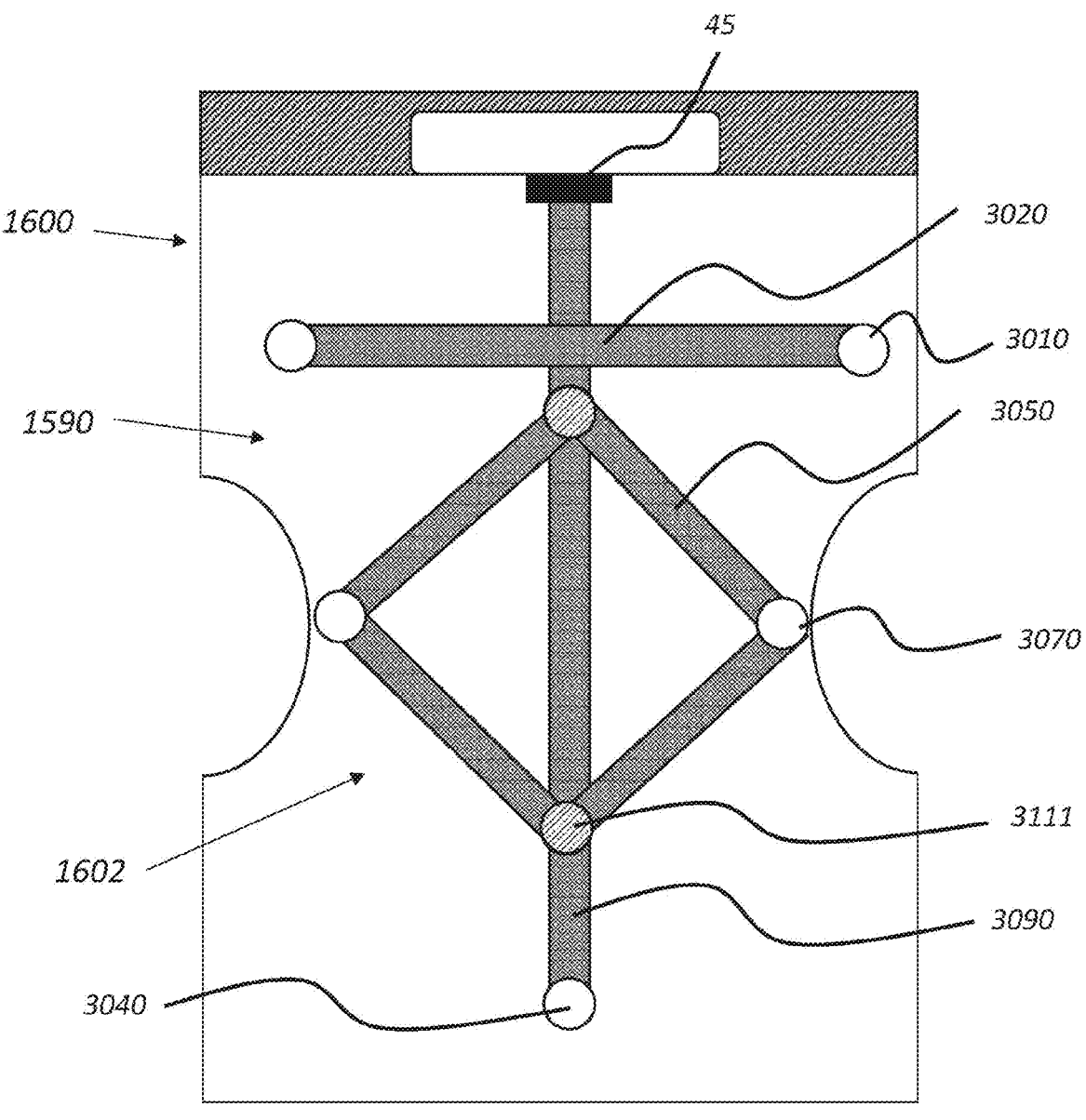
Figure 5:
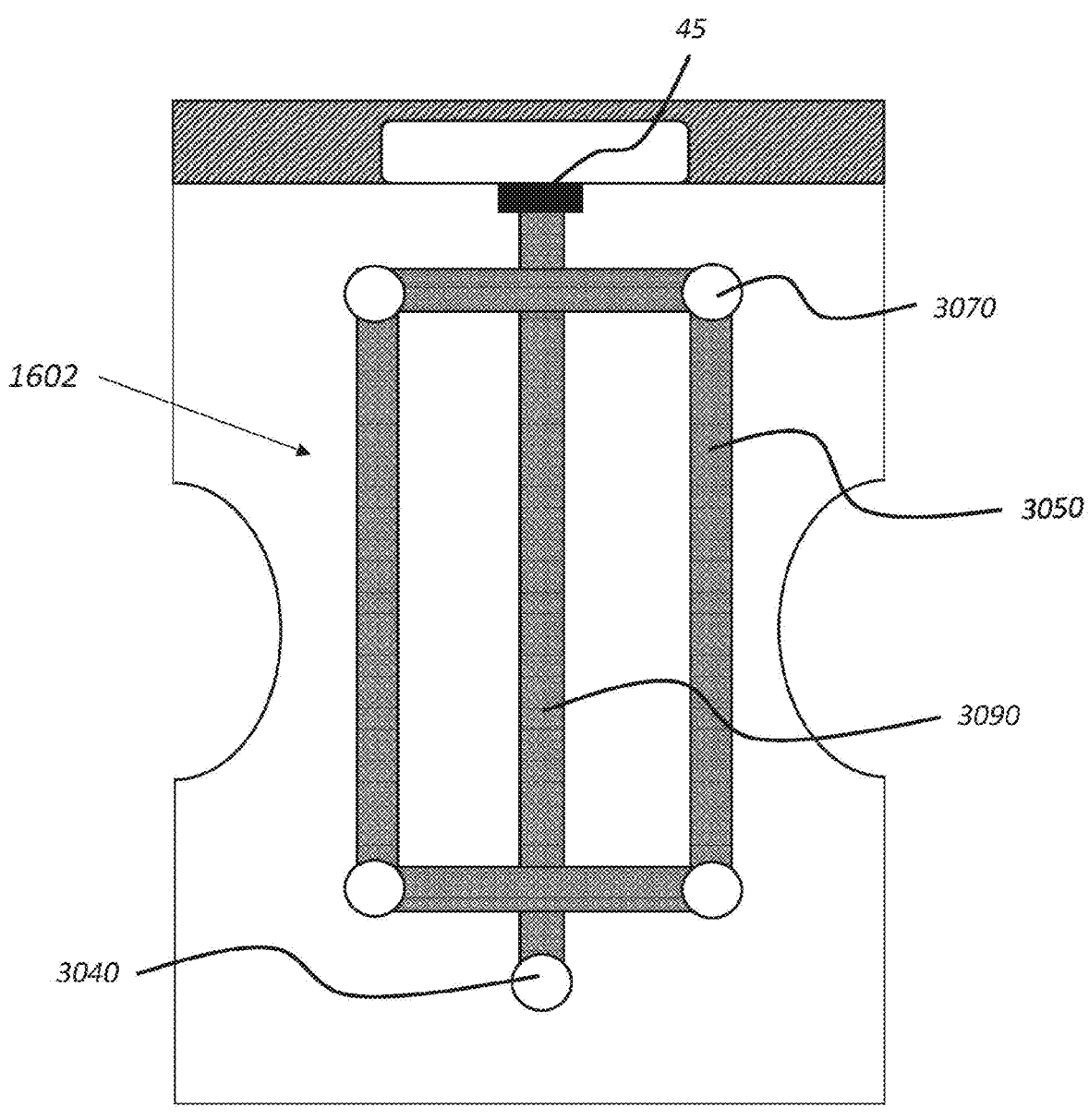
Figure 6:
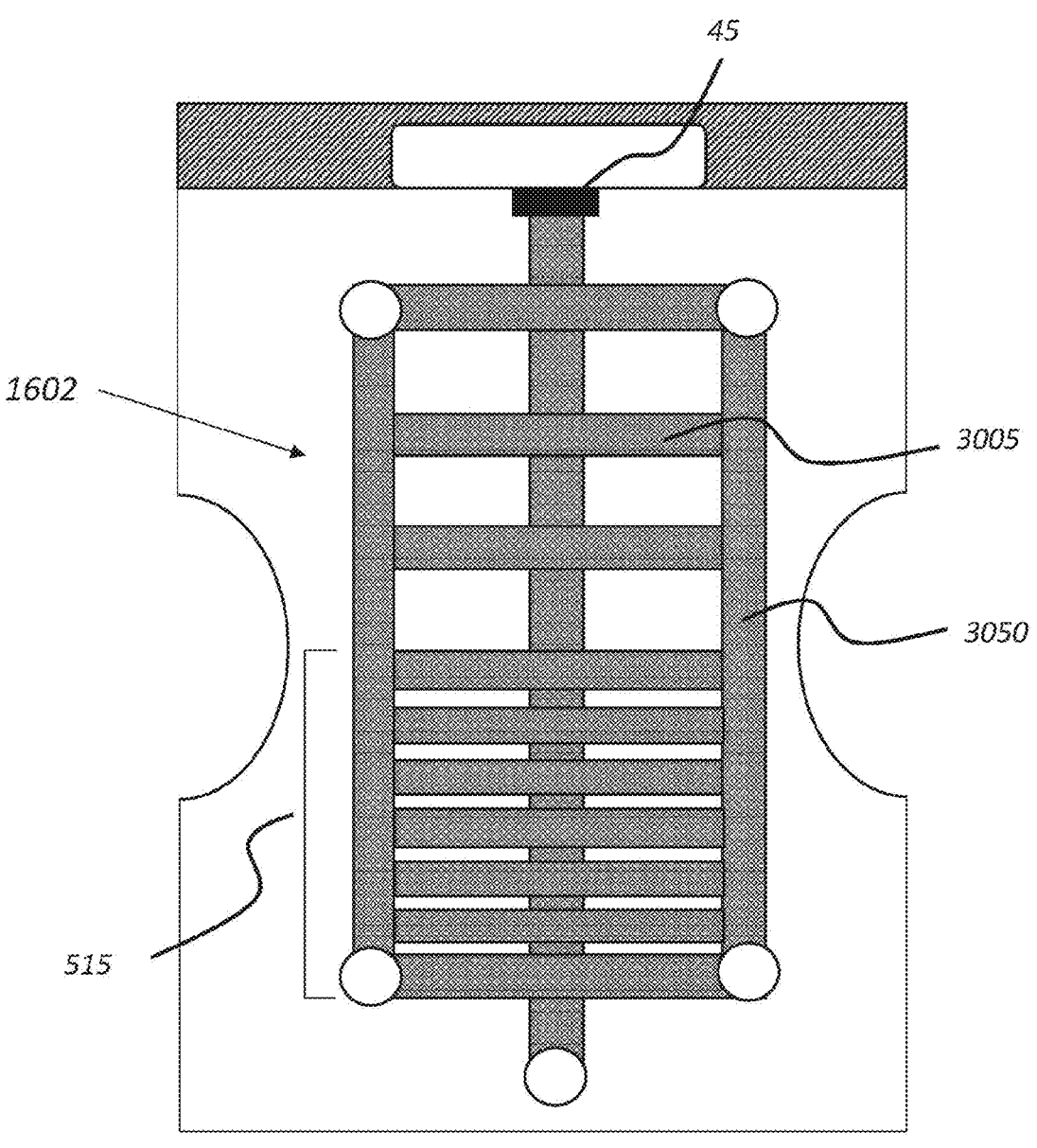

FIGS. 4-6 show further alternative configurations of expandable members of sensing devices. In these configurations, the elastic elements of the expandable member comprise multiple elastic elements arranged in a polygon with attachments points at one or more corners of the polygon. For example, in FIG. 4, the multiple elastic elements 3050 are arranged in a diamond shape with two attachment points 3070 at two corners of the diamond. These two attachment points 3070 are positioned in the crotch region 1540—one near to the left elasticated edge 1560, and the other near to the right elasticated edge—and are fixedly attached to the external surface 1590 of the nappy 1600. There are also two junction points 3111 (shown by hashed circles in FIG. 4) connected to the expandable elements 3050 at the other two corners of the diamond. The two junction points 3111 are not attached to the external surface 1590 of the nappy 1600, and are therefore free to move as the nappy 1600 expands. One of the two junction points 3111 is a front junction point positioned centrally over the front 1530 of the nappy 1600, the other is a back junction point positioned centrally over the back 1570 of the nappy 1600. The diamond is positioned centrally and predominately on the crotch region 1540 of the nappy 1600, and extends partially across the front 1530 and back 1570 of the nappy 1600. There is also a longitudinal elastic element 3090 positioned centrally on the nappy 1600 (similar to longitudinal elastic element 4010 of FIG. 2). The longitudinal elastic element 3090 is attached to the nappy 1600 between a back attachment point 3040, positioned centrally on the back 1570 of the nappy 1600, and the detector unit attachment point 45, positioned centrally on the front 1530 of the nappy 1600, next to the detector unit 5. Both the back attachment point 3040 and the detector unit attachment point 45 are fixedly attached to the external surface 1590 of the nappy 1600. The longitudinal elastic element 3090 is also connected to the front and back junction points 3111. There may also be additional elastic elements 3020 connected to the longitudinal elastic element 3090, and attached to the external surface 1590 of the nappy 1600 by attachment points 3010. For example, in FIG. 4, an additional elastic element 3020 is attached to the external surface 1590 of the nappy 1600 by attachment points 3010 on the front 1530 and near to the elasticated edges 1560 of the nappy 1600, perpendicularly across the longitudinal elastic element 3090.

As shown in FIG. 5, there is again a central longitudinal elastic element 3090 attached to the nappy 1600 between the detector unit attachment point 45 and the back attachment point 3040. The back attachment point 3040 is positioned centrally on the back 1570 of the nappy 1600, as in FIG. 4. The central elastic element 3090 is also connected to at least one of the multiple elastic elements 3050 arranged in a polygon. In FIG. 5, the multiple elastic elements 3050 are arranged in a rectangle, with an attachment point 3070 at each corner of the rectangle. In this configuration, each of the attachment points 3070, 3040, 45 are fixedly attached to the external surface 1590 of the nappy 1600, near to edges of the nappy 1600. The rectangle is positioned in a substantially similar location to the elastic patch 1604 of FIG. 1. In particular, the rectangle is positioned with a first transverse elastic element across the front 1530 of the nappy 1600, substantially parallel to the waistband of the nappy 1600. There are two longitudinal elastic elements running substantially perpendicular from the first transverse elastic element, across the crotch region 1540, and to the back 1570 of the nappy 1600. There is also a second transverse elastic element across the back 1570 of the nappy 1600, substantially parallel to the first transverse element. Any suitable polygon configuration may also be used, such as a square, pentagon, hexagon and so on.

FIG. 6 shows the same configuration of the expandable member 1602 as FIG. 5, except that in FIG. 6 the expandable member 1602 further comprises transverse elastic elements 3005 extending between the two longitudinal elastic elements. In addition, the transverse elastic elements are concentrated within a specified area 515 of the polygon. For example, in FIG. 6, the specified area 515 is a substantial part of the crotch region 1540 and a substantial part of the back 1570 of the nappy 1600. The transverse elements 3005 are concentrated in this area 515 so as to provide more sensitivity when detecting expansion of the nappy 1600. When urine (for example, 50 to 100 ml) initially ingresses the nappy 1600, expansion of the nappy 1600 first occurs in this region 515. However, the expansion may be very small.

The transverse elastic elements 3005 allow the expansion force in this region 515 to be captured more accurately. Alternatively, as shown in FIG. 1, the elastic elements may include an elastic patch which serves a similar purpose.

Figure 7:
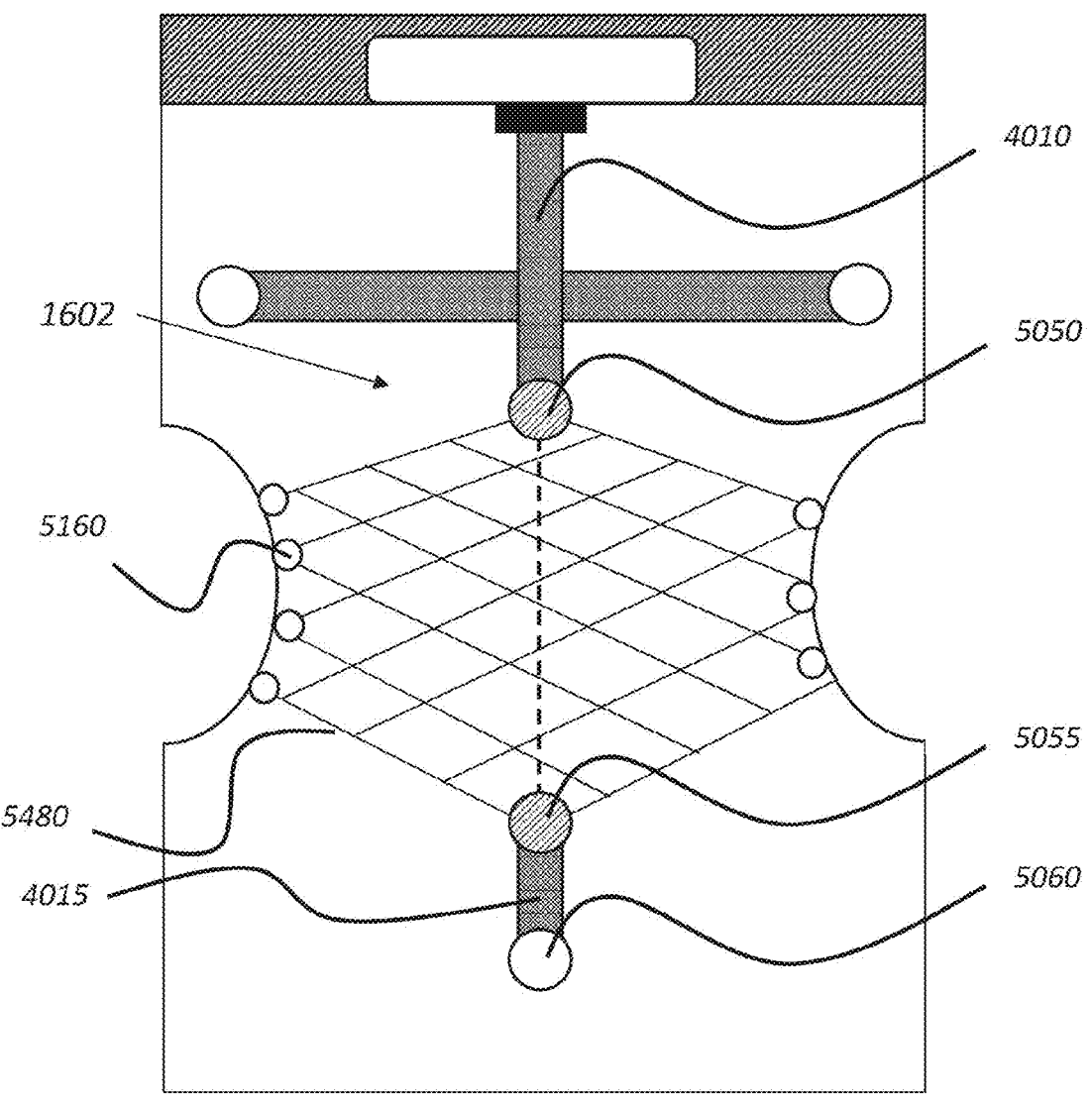

FIG. 7 shows another alternative configuration of the expandable member 1602 of a sensing device. In this configuration, the elastic elements include an elastic net 5480, and the attachment points comprise attachment points 5160 at a periphery of the elastic net 5480. The attachment points also comprise a detector unit attachment point 45 (similar to the detector unit attachment point 45 described above) positioned centrally on the front 1530 of the nappy 1600, next to the detector unit 5 (which is mounted on the waistband of the nappy 1600). The elastic elements also include a longitudinal elastic element 4010 positioned centrally on front 1530 of the nappy 1600. The longitudinal elastic element 4010 extends between a front junction point 5050, positioned centrally over the front 1530 of the nappy 1600, and the detector unit attachment point 45. The front junction point 5050 (shown by a hashed circle in FIG. 7) is not attached to the external surface 1590 of the nappy 1600, and is therefore free to move as the nappy 1600 expands. The detector unit attachment point 45 is fixedly attached to the external surface 1590 of the nappy 1600. The elastic net 5480 is connected to the central longitudinal elastic element 4010 by the front junction point 5050. The elastic net 5480 is also attached to a back junction point 5055, positioned centrally over the back 1570 of the nappy 1600. The back junction point 5055 (also shown by a hashed circle in FIG. 7) is not attached to the external surface 1590 of the nappy 1600, and is therefore free to move as the nappy 1600 expands. A short elastic element 4015 extends from the back junction point 5055 to another attachment point 5060 positioned further up the back 1570 of the nappy 1600. The attachment point 5060 is fixedly attached to the external surface 1590 of the nappy 1600. The attachment points 5160 at a periphery of the elastic net 5480 are positioned along the elasticated edges 1560 of the nappy 1600, i.e., the attachment points 5160 are positioned on the two curved edges of the crotch region 1540 where the nappy 1600 is contoured around the wearer's legs. The attachment points 5160 are fixedly attached to the external surface 1590 of the nappy 1600. In between the attachment points 5160 and the junction points 5050, 5055 the elastic net 5480 is free to stretch. The elastic net 5480 may cover a substantial part of the crotch region 1540 of the nappy 1600. For example, the elastic net 5480 may be sized and configured to extend across a full width of the crotch region 1540 of the nappy 1600, as shown in FIG. 7. In an alternative example, the elastic net 5480 may also cover a substantial part of the front 1530 and back 1570 surface of the nappy 1600. Advantageously, using an elastic net 5480 allows greater forces (from the expanding nappy 1600) to be captured and transmitted to the central elastic element 4010 so as to be detected by the detector unit.

Figure 8:
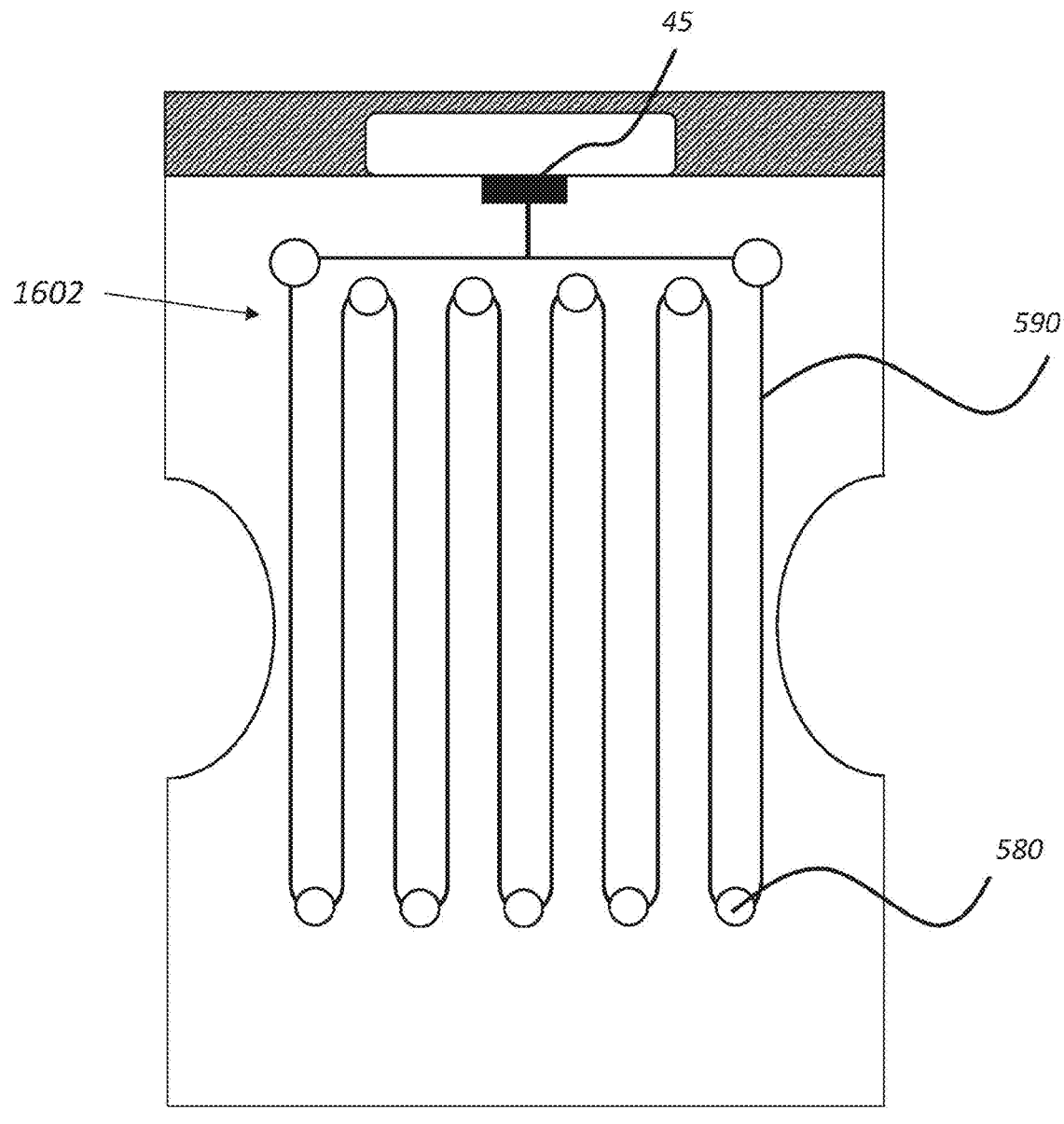

FIG. 8 shows another alternative configuration of the expandable member 1602 of a sensing device. In this configuration, attachment points 580 are connected via one or more elastic elements 590 so as to form a meandering pattern, the attachment points 580 are positioned at each turn of the meandering pattern. The detector unit 5 is mounted on the waistband section of the nappy 1600. The attachment points also include a detector unit attachment point 45 positioned centrally on the front of the nappy 1600, next to the detector unit 5. The other attachment points 580 comprise six front attachment points disposed approximately linearly and transversely across the front of the nappy 1600, and five back attachment points disposed approximately linearly and transversely across the back of the nappy 1600. The six front attachment points are fixedly attached to the external front surface of the nappy 1600 near to a front upper edge of the nappy (i.e., near to the waistband). The five back attachment points are fixedly attached to the external back surface of the nappy 1600 near to a back upper edge of the nappy (i.e., near to the back waistband). One of the elastic elements 590 extends down from the central detector unit attachment point 45 and transversely across the front of the nappy 1600 towards the two outer front attachment points 580. The remaining elastic elements 590 extend substantially longitudinally (lengthways) in a meandering pattern over the external surface of the nappy 1600. In particular, two further elastic elements 590 extend longitudinally (lengthways), from each of the two outer front attachment points 580 down the front, crotch region and up the back of the nappy 1600 to reach the two outer back attachment points 580. The elastic elements 590 then connect to the remaining attachment points 580 in a meandering configuration between the front attachment points and the back attachment points, with an attachment point at each turn. The elastic elements 590 are free to stretch between the attachment points 580, 45 as the nappy 1600 expands. The elastic elements 590 are thinner than the elastic elements of FIGS. 1-7, so as to allow the elastic elements 625 to meander more easily. For example, in FIG. 8, the elastic elements 625 may be made from thin strips or threads or wires of elastic material. FIGS. 4-8 relate to examples where the sensing device is attached to the external surface of the nappy after the nappy has been manufactured, and examples where the expandable member of the sensing device is integrated onto the external surface of the nappy during manufacture.

In use, in all of the above described configurations, the detector unit 5 may be configured to detect expansion of the expandable member 1602 by sensing a relative displacement between the detector unit attachment point 45 and at least one other attachment point. For example (see FIG. 2), as the nappy 1600 expands, attachment point 4080 may be moved away from detector unit attachment point 45, producing a relative displacement between the attachment points 45, 4080. The relative displacement between the detector unit attachment point 45 and the at least one other attachment point 4080 causes the expandable member 1602 to pull the detector unit attachment point 45 in a direction away from the detector unit 5. This causes a proportional pull on the detector unit 5, resulting in a change in a detected signal produced in the detector unit 5. In other words, the detector unit detects a pull on the detector unit caused by expansion of the nappy. The change in the detected signal is proportional to the overall volume expansion of the nappy 1600, due to the ingress of urine and/or feces inside it. Different examples for detecting expansion of the expandable member 1602 will now be described.

Optical Detectors

Figure 9A:
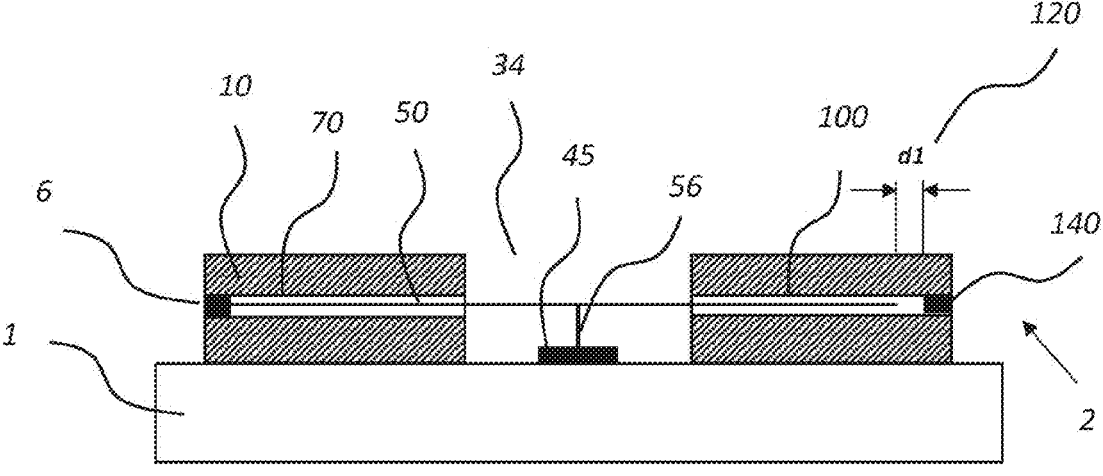
FIG. 9$a$ is a cross-sectional view of an exemplary optical detector for use with the sensing device of any of FIGS. 1-8.
Figure 9B:
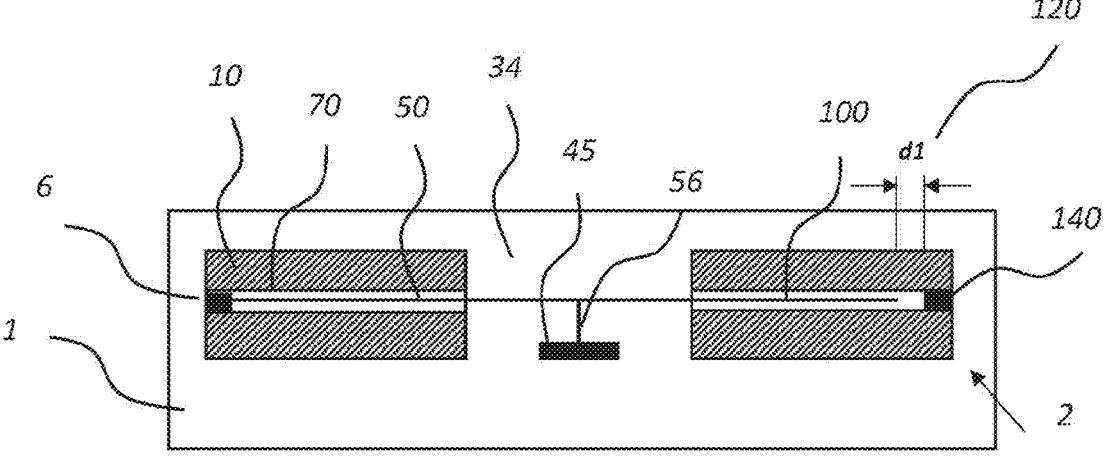

FIGS. 9a-9d show an example of a detector unit 2 comprising an optical detector, for use with any of the sensing devices described above. FIGS. 9a and 9b respectively show cross-sectional front and plan views of the detector unit 2 positioned on a nappy 1 in an unexpanded state—the nappy 1 is worn on the body but is not being used, i.e. there is no urine and/or feces in the nappy 1, therefore there is no additional stretch in the nappy 1 (except that required to fit the nappy to the wearer, e.g., stretch of the elasticated edges around the top of the wearer's legs, and stretch of the waistband, which is elasticated). The nappy 1 is equivalent to the nappy 1600 described above with respect to FIGS. 1-8.

The detector unit 2 comprises a housing 10, a light source 6, a light detector 140, a first tube 70, a second tube 100, an optical fibre 50, and a link 56 to the detector unit attachment point 45 of the expandable member (e.g., expandable member 1602 as per FIGS. 1-8 above). For simplicity, the expandable member is not show in FIGS. 9a-9d except by virtue of the detector unit attachment point 45. The light source 6 may be a light-emitting diode (LED). The light detector 140 may be a photodetector. The housing 10 is mounted on the nappy 1. For example, the housing 10 may be mounted on the waistband of the nappy 1.

The housing 10 is a two-part housing, and the two parts of the housing 10 are separated by an opening 34. The housing 10 has two ends—one at a far end of the first part of the housing 10, and the other at a far end of the second part of the housing 10. The light source 6 is mounted at one end of the housing 10, and the light detector 140 is mounted at the other end of the housing 10, opposite to the light source 6. The first tube 70 and the second tube 100 are mounted coaxially in the housing 10, along respective portions of a path between the light source 6 and the light detector 140. As such, the first tube 70 is positioned within the first part of the housing 10, and the light source 6 is positioned at a first end of the first tube 70. The second tube 100 is positioned within the second part of the housing 10, and the light detector 140 is positioned at a second end of the second tube 100. The two parts of the housing 10, and the first tube 70 and the second tube 100, are spaced apart (for example, up to 4 cm) by the opening 34. Similarly, the first tube 70 and the second tube 100 are also spaced apart by the opening 34.

The optical fibre 50 extends through the first tube 70 and the second tube 100. A first end of the optical fibre 50 is positioned adjacent to, and fixed in front of, the light source 6. A second end of the optical fibre 50 is located near to the light detector 140, but is not fixed in position. There a gap 120 between the second end of the optical fibre 50 and the light detector 140. At least a central part of the optical fibre 50 is exposed in the opening 34 between the tubes 70, 100 (i.e., the central part of the optical fibre 50 is not contained within either of the tubes 70, 100, or within the housing 10). The internal diameter of the tubes 70, 100 is preferably slightly larger than the outer diameter of the optical fibre 50, so that movement of the optical fibre 50 within the tubes 70, 100 is somewhat restricted and so that the optical fibre 50 largely remains in position in use.

As discussed previously, the detector unit attachment point 45 forms part of the expandable member; the remainder of the expandable member is not shown in FIGS. 9a-9d. The detector unit attachment point 45 is used to connect the expandable member to the detector unit 2. In particular, a non-elastic link 56 extends between the detector unit attachment point 45 and the exposed part of the optical fibre 50.

In use, power is supplied to the detector unit 2 by an electronic control and power supply unit (not shown). The electronic control and power supply unit may be an internal or external power supply, such as a battery. The supply of power to the detector unit 2 causes light from the light source 6 to travel through the optical fibre 50 and the gap 120 to the light detector 140. The light detector 140 is configured to generate an output signal corresponding to the amount of light received from the light source 6. When the nappy 1 is being worn, and the nappy 1 is in the unexpanded state (i.e., no urine and/or feces inside the nappy 1, as per FIGS. 9*a* and 9*b*), the expandable member and the link 56 are minimally taut, and the light detector 140 produces an output signal that corresponds to the unexpanded state of the nappy 1. In this unexpanded state, the gap 120 has a length dl.

Figure 9C:
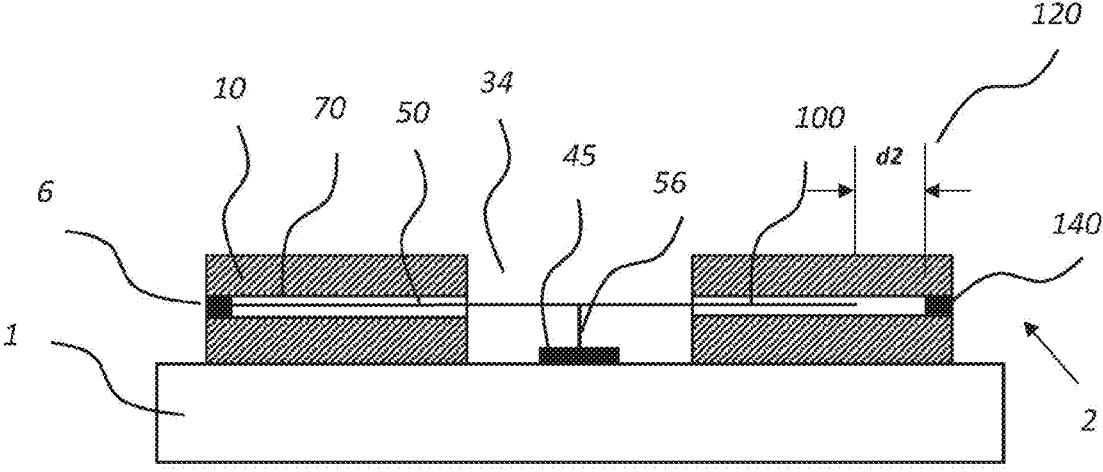
Figure 9D:
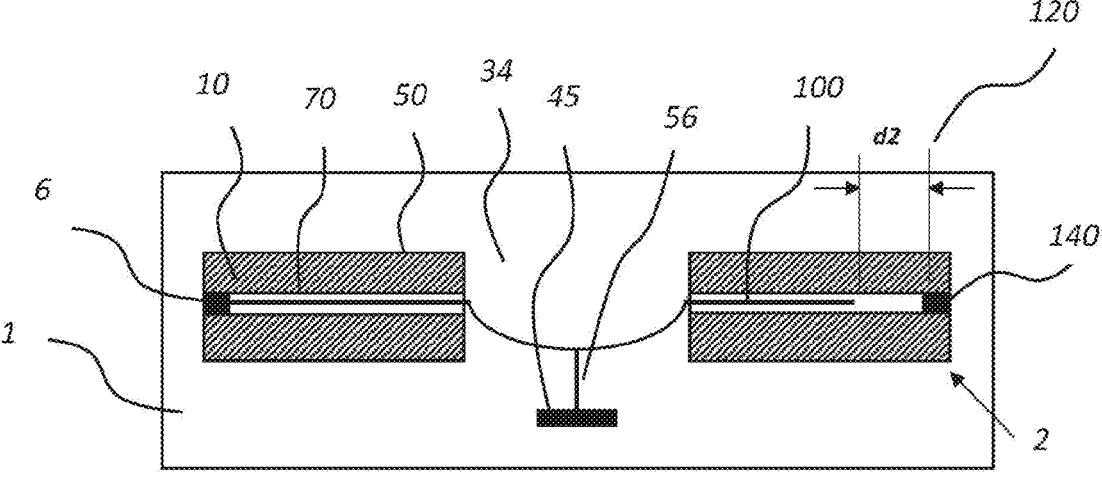

FIGS. 9*c* and 9*d* show cross-sectional front and plan views of the detector unit 2 and nappy 1 in an expanded state—as the nappy 1 begins to fill with urine and/or feces, and starts to expand (i.e., the volume of the nappy 1 expands). This results in expansion of the expandable member which is attached to the external surface of the nappy 1. As mentioned, the expandable member is not show in FIGS. 9*a*-9*d* except by virtue of the detector unit attachment point 45. This expansion is measured by the detector unit 2. The detector unit 2 is configured such that an amount of light reaching the light detector 140 from the light source 6 varies in dependence on the relative displacement between the detector unit attachment point 45 and at least one other attachment point (e.g., the relative displacement between attachment point 4080 and detector unit attachment point 45 in FIG. 2), thereby producing a change in an output signal from the light detector 140. In other words, as the nappy 1 expands, the attachment points of the expandable member are displaced from each other, causing the elastic element(s) of the expandable member to stretch (e.g., longitudinal elastic element 4010 in FIG. 2). In turn, this creates a pull on the detector unit attachment point 45 and the link 56. The link 56 pulls the exposed central portion of the optical fibre 50 in the direction of the detector unit attachment point 45, i.e., away from the housing 10 of the detector unit 2, such that the optical fibre 50 deflects. The optical fibre 50 is constrained to move only when a force is applied to the optical fibre 50 by the expandable member. The optical fibre 50 deflection is most clearly seen in FIG. 9*d* and results in a change in the gap 120 between the second end of the optical fibre 50 and the light detector 140. As the second end of the optical fibre 50 is not fixed in position, it is free to move longitudinally through the second tube 100, thereby allowing the change in the gap 120. The gap 120 increases from dl (in the unexpanded state of FIGS. 9*a* and 9*b*) to a larger value d2 (in the expanded state of FIGS. 9*c* and 9*d*). This increase in the gap 120 reduces the amount of light received by the light detector 140 from the light source 6. The proportion of the emitted light that strikes the light detector 140 reduces with increasing size of the gap 120. Therefore, the output signal produced by the light detector 140 decreases when there is ingress of urine and/or feces inside the nappy 1, indicating that the nappy 1 has expanded. In particular, the light signal received by the light detector 140 is inversely proportional to the nappy expansion. Based on this, a nappy fullness parameter can be determined.

Similarly, if the expansion in the nappy 1 is reduced (for example, due to leakage of urine from the nappy 1), the pull on the exposed central portion of the optical fibre 50 is reduced. As such, the exposed portion of the optical fibre 50 moves back in a direction away from the detector unit attachment point 45, i.e., toward the detector unit 2. This causes the gap 120 between the optical fibre 50 and the light detector 140 to decrease. This increases the amount of light received by the light detector 140 from the light source 6 via the optical fibre 50. Therefore, the output signal produced by the light detector 140 increases, indicating that the nappy 1 has shrunk.

The change in gap 120 depends on the properties of the material from which the nappy 1 is made, the material properties of the expandable member, and the properties of the optical fibre 50. The deflection of the optical fibre 50 in the exposed region in the direction of pull is expressed by the equation:

$$\delta = \frac{FL^3}{48EI} \tag{1}$$

where δ is the deflection of the optical fibre 50 in the direction of the pull (i.e., the stretch distance in the direction of the pull), F is the pulling force in the link 56, L is the length of the exposed central region of the optical fibre 50, E is the Young's Modulus of the material of the optical fibre 50, and I is the moment of inertia of the optical fibre 50. When the nappy 1 expands, the force F exerted on the optical fibre 50 by the link 56 increases, thus increasing the deflection 8 of the optical fibre 50 according to equation (1). This deflection results in an increased distance d2 between the second end of the optical fibre 50 and the light detector 140. As the intensity of the light received by the light detector 140 is proportional to $1/d^2$, the output signal produced by the light detector 140 decreases. Therefore, since the gap distance d is directly proportional to the deflection 8 of the optical fibre 50, it follows that the output of the light detector 140 is inversely proportional to the square of the deflection (i.e., proportional to $1/\delta^2$).

In an alternative example, the second end of the optical fibre 50 may be fixed in front of the light detector 140, and the first end of the optical fibre 50 may be located adjacent to the light source 6, but not fixed in position, thereby enabling it to move longitudinally within the first tube 70. As such, the gap 120 will be positioned between the light source 6 and the first end of the optical fibre 50. Equation (1) applies analogously in this example.

Figure 10:
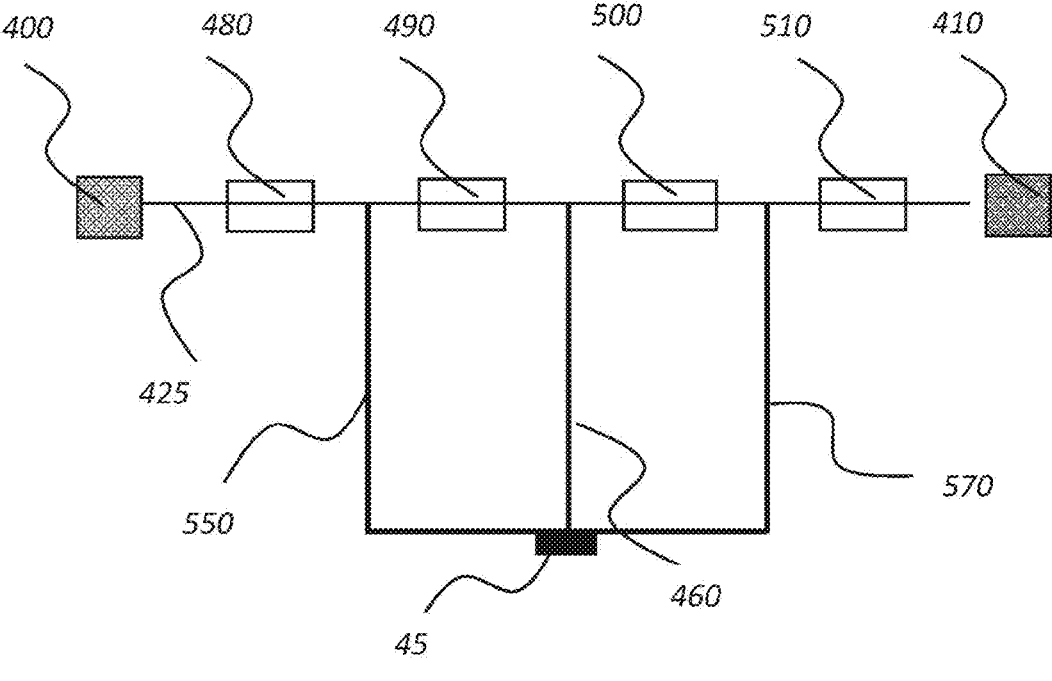
FIG. 10 is a plan view of an alternative exemplary optical detector for use with the sensing device of any of FIGS. 1-8. The optical detector comprises a plurality of links.

FIG. 10 is an alternative example of the optical detector unit 2 of FIGS. 9*a*-9*d*. Like the optical detector of FIGS. 9*a*-9*d*, a light source 400 injects light into an optical fibre 425 at a first end of the optical fibre 425. The first end of the optical fibre 425 is fixed relative to the light source 400. The light travels through the optical fibre 425 to a light detector 425, which is positioned at a second end of the optical fibre 425. The second end of the optical fibre 425 is not fixed in position relative to the light detector 410. The optical fibre 425 provides a substantially linear path between the light source 400 and the light detector 410 in FIG. 10. However, in FIG. 10, there are four tube sections 480, 490, 500 and 510 positioned along respective portions of the substantially linear path between the light source 400 and the light detector 410 through which the optical fibre 425 passes. The tube sections 480, 490, 500, 510 act as guides for the optical fibre 425. There are openings between the four tube sections 480, 490, 500 and 510 to expose three portions of the optical fibre 425. Three links 550, 460, 570 couple the detector unit attachment point 45 to the three exposed portions of the optical fibre 425. It will be understood that the use of four tube sections and three links is merely exemplary—a different number of tube portions (e.g. 3 or more) could be used to provide a different number of exposed portions of the optical fibre 425 (e.g. 2 or more). The number of links used corresponds to the number of exposed portions of the optical fibre 425. Advantageously, having multiple, separately spaced links 550, 460, 570 allows the optical fibre 425 to be more uniformly pulled along its length by the detector unit attachment point 45. As such, this configuration is more stable and generates greater deflection 8.

Figure 11A:
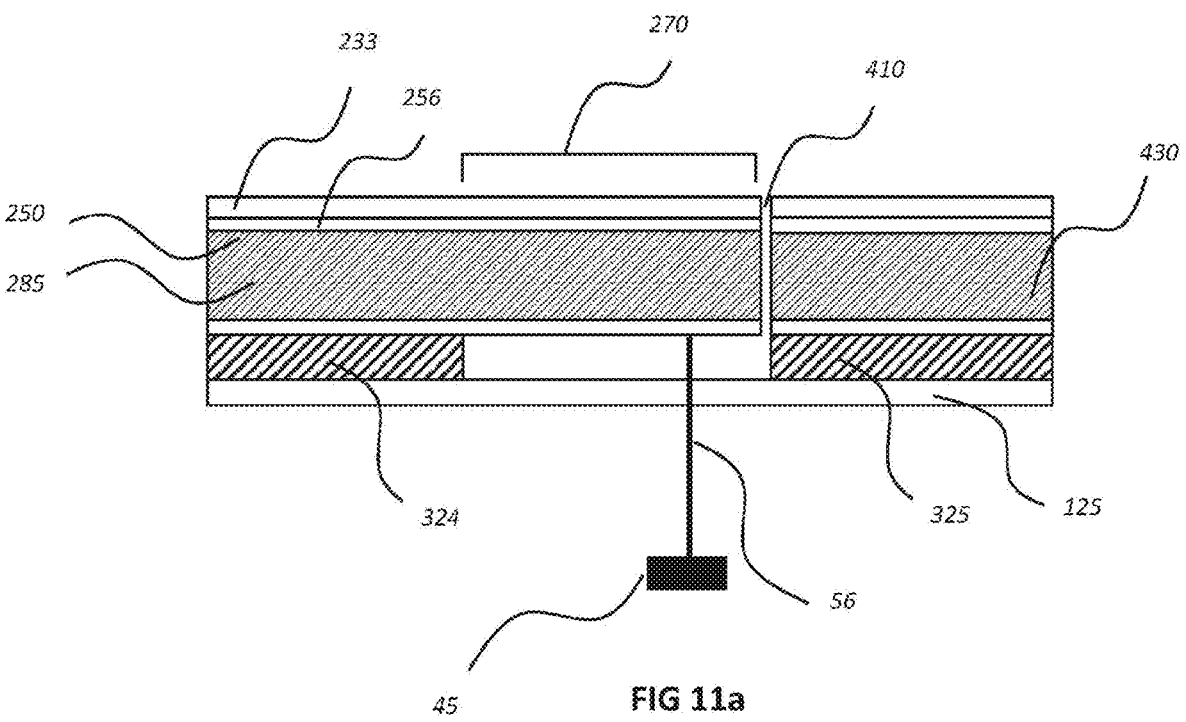
FIG. 11$a$ is a cross-sectional view of an alternative exemplary optical detector for use with the sensing device of any of FIGS. 1-8.
Figure 11B:
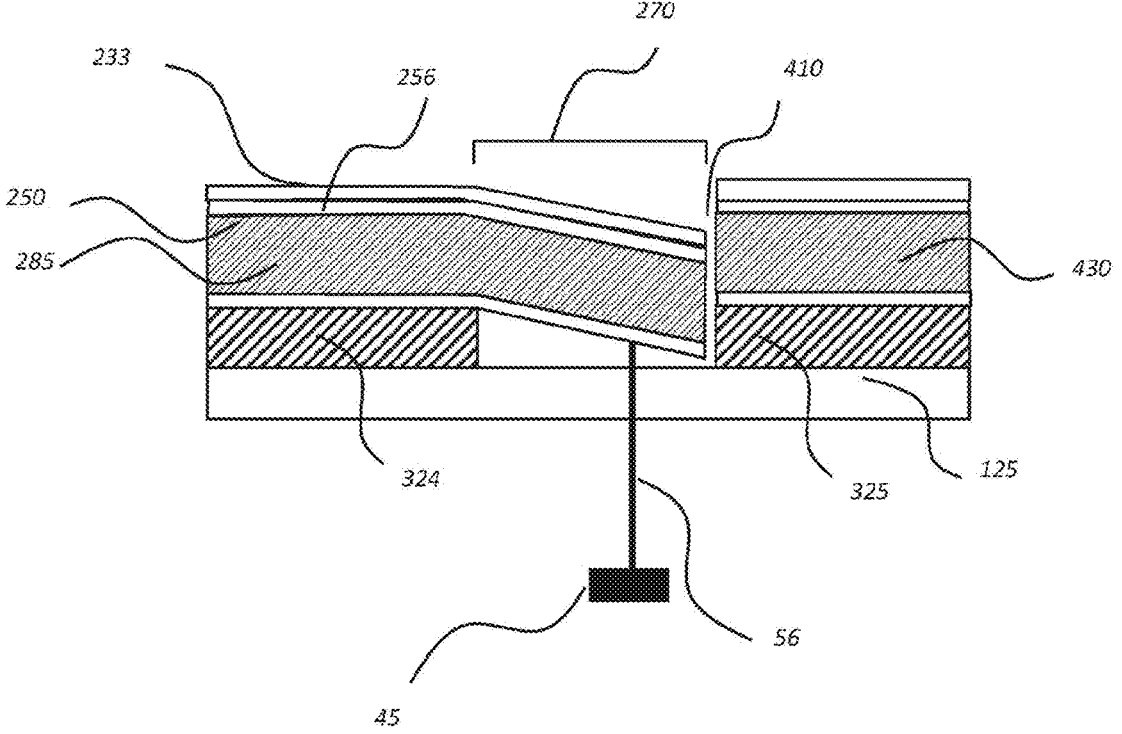

FIGS. 11a and 11 b show a further alternative example of an optical detector unit configured for use with any one of the sensing devices described above. For simplicity, the expandable member is not show in FIGS. 11a-11b except by virtue of the detector unit attachment point 45. In FIGS. 11a and 11b, the optical detector unit comprises a laminated structure having the following layers from top to bottom (as shown in FIG. 11a): a lamination layer 233, an optical fibre in two coaxial sections 285 and 430 separated by an air gap 410, a rigid spacer comprising two portions 324, 325 separated by a spacer gap, and a flexible substrate 125. The optical fibre comprises a fibre core 250 and fibre cladding 256, as is well known. The lamination layer 233 is a thin flexible plastic layer to protect the top of the laminated structure. The air gap 410 between the two coaxial sections 285 and 430 is positioned above, and next to, a first end of the rigid spacer portion 325. The first end of the rigid spacer portion 325 is vertically in line with a first end of the coaxial section 430 of the optical fibre, and is horizontally adjacent to the spacer gap. As such, a section 270 of the first optical fibre section 285 is free standing and able to bend when a force is applied. The free standing section 270 of the first optical fibre section 285 is connected to the detector unit attachment point 45 via a non-elastic link 56. Whilst FIGS. 11a and 11 b show a cross-sectional view of the optical fibre, rigid spacer and flexible substrate 125, the link 56 actually extends out substantially perpendicular from the optical fibre to the detector unit attachment point 45 (i.e. it extends out substantially in the plane of the external surface of the nappy). The detector unit attachment point 45 is part of the expandable member (e.g., one of expandable member 1602 described above). The expandable member is fixedly attached to the external surface of the nappy (e.g., nappy 1600).

The detector unit of FIG. 11a may be manufactured by placing the rigid spacer on the flexible substrate 125, placing a single optical fibre on the rigid spacer, and then placing a lamination layer 233 on top of the optical fibre. Next, the lamination layer is laminated onto the top of the structure (for example, using heat or ultrasound). A vertical cut is made in the free standing section 270 of the optical fibre using a sharp device (e.g. a blade) to form the air gap 410 at one end of the spacer gap such that the air gap 410 and the spacer gap form a single air space. The vertical cut, and thus the air gap 410, extends through each of the lamination layer 233, the fibre cladding 256, and the fibre core 250, thereby separating the optical fibre into the two coaxial sections 285 and 430. The vertical cut does not extend through the substrate 125. A far (left) end (not shown) of the first optical fibre section 285 is coupled to a light source (not shown) and a far (right) end of the second optical fibre section 430 is coupled to a light detector (not shown).

In use, when the light source shines light into the far end of the first optical fibre section 285, the light travels through the air gap 410 and into the second optical fibre section 430. FIG. 11 a shows the configuration of the detector unit when the nappy is in an unexpanded state. In this configuration, the expandable member and the non-elastic link 56 are minimally taut, and the light detector produces an output signal that corresponds to the unexpanded state of the nappy. There is a small loss (e.g., in the region of 20%) in light transmission due to the air gap 410.

FIG. 11 b shows the configuration of the detector unit when the nappy is in an expanded state. In this configuration, the detector unit attachment point 45 is further away from the detector unit due to expansion of the nappy causing the expandable member to pull on the detector unit attachment point 45. As the link 56 is non-elastic, the pull from the expandable member is transferred to the optical fibre, thereby pulling the free-standing section 270 of the optical fibre away from second optical fibre section 430. This pull causes the optical fibre sections 285, 430 to become misaligned. The signal transmission therefore drops dramatically (up to 80%). The larger the pull, the more the signal drops at the light detector. The drop in signal is directly proportional to the volume expansion of the nappy as more and more urine and/or feces ingress the nappy. The sensitivity of the optical detector unit depends on the material properties of the optical fibre and the rigid spacer, the force applied by the detector unit attachment point 45, and the dimension of the free standing section 270 of the optical fibre.

Figure 12:
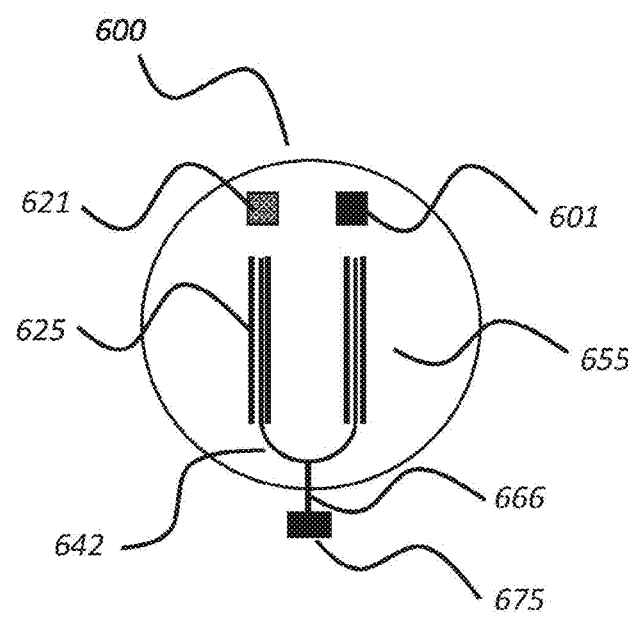
FIG. 12 is a plan view of an alternative optical detector for use with the sensing device of any of FIGS. 1-8.

FIG. 12 shows an alternative example of an optical detector unit for use with any one of the sensing devices described above. In this configuration, the detector unit 600 is constructed on a small footprint circular printed circuit board 655. The detector unit 600 comprises a light source 621 (such as a light-emitting diode), a light detector 601 (such as a photodetector), an optical fibre 642, two linear guide rails 625, and a link 666 which connects the optical fibre 642 to a detector unit attachment point 675. The detector unit attachment point 675 may be equivalent to the detector unit attachment point 45 described previously, and is one of the attachment points of the expandable member (e.g., expandable member 1602). For simplicity, the expandable member is not show in FIG. 12 except by virtue of the detector unit attachment point 675.

The light source 621 is positioned near one edge of the printed circuit board 655. The light detector 601 is positioned next to the light source 621. The optical fibre 642 is positioned in a U shape across a substantial area of the printed circuit board 665. A first end of the optical fibre 642 is placed in front of the light source 621, such that there is a first gap between the first end of the optical fibre 642 and the front of the light source 621. A second end of the optical fibre 642 is placed in front of the light detector 601, such that there is a second gap between the second end of the optical fibre 642 and the front of the light detector 601. The two linear guide rails 625 are positioned in parallel on the printed circuit board 655 to guide the two straight line sections of the U-shape of the optical fibre 642; one guide rail forms a first straight line leading to the light source 621, and the other guide rail forms a second straight line leading to the light detector 601. The optical fibre 642 passes through each guide rail 625. The guide rails 625 are configured to keep the optical fibre 642 aligned with a respective optical axis of each of the light source 621 and the light detector 601. The link 666 is connected centrally to the optical fibre 642 at the bottom of the U shape.

The light source 621 shines light into the optical fibre 642. The light travels through the U shaped optical fibre 642 and is detected by the light detector 601. When the expandable member exerts a pull on the detector unit attachment point 675, in a direction away from the detector unit 600, the optical fibre 642 is moved further away from the light source 621 and/or the light detector 601, thereby increasing the size of the first gap and/or the second gap. This causes the detected signal to reduce. The drop in the detected signal is proportional to the pull, which is proportional to the volume of urine and/or feces inside the nappy (e.g., nappy 1600).

Hence, the change in the detected signal is indicative of the expansion of the nappy.

So far, only one sensing device attached to a nappy has been shown. However, any suitable number of sensing devices may be used on the same nappy.

Figure 13:
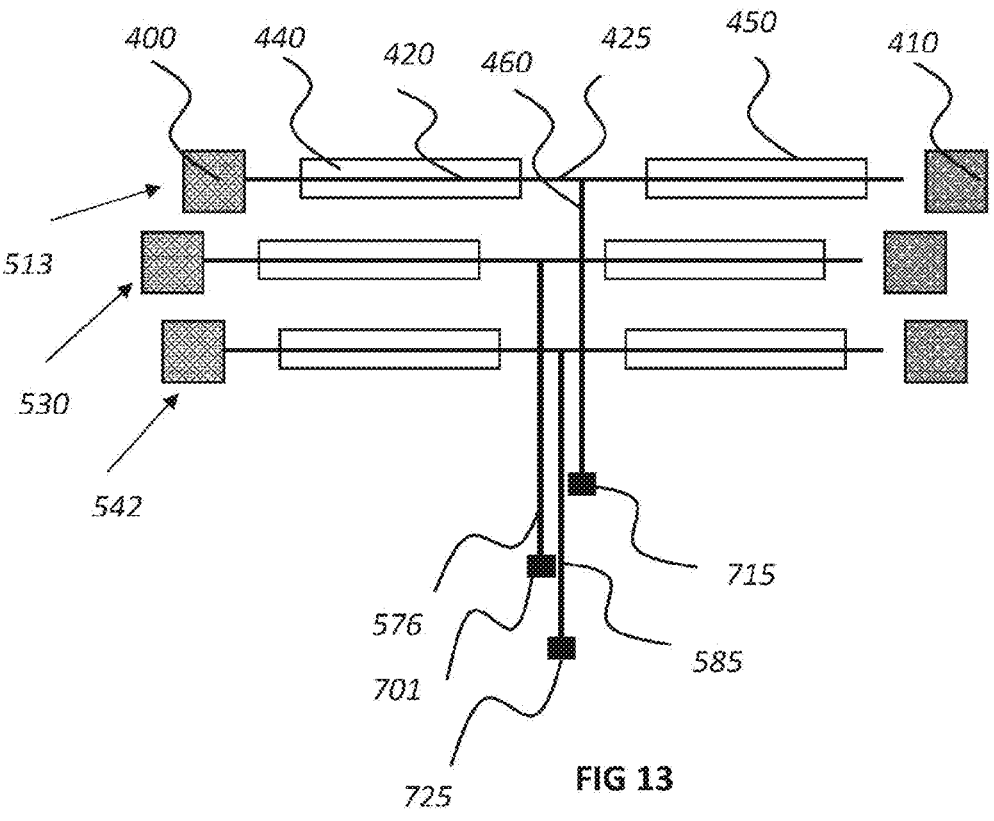
FIG. 13 is a plan view of a plurality of exemplary optical detectors for use with the sensing device of any of FIGS. 1-8.

For example, the nappy may be combined with one or more additional sensing devices. The sensing device and the one or more additional sensing devices are configured to detect expansion at different locations on the external surface of the nappy. In FIG. 13, there is a first detector unit 513, a second detector unit 530, and a third detector unit 542. The three detector units 513, 530, 542 are each equivalent to the detector unit described in FIGS. 9a-9d, and work in the same manner. For example, the first detector unit 513 comprises a light source 400, an optical fibre 425, a first tube 440, a second tube 450, a light detector 410, and a link 50 that connects the optical fibre 425 to a detector unit attachment point 715. Detector unit attachment point 715 may be equivalent to detector unit attachment point 45 described previously. The detector unit attachment point 715 forms part of an associated expandable member; the remainder of the expandable member is not shown in FIG. 13.

Each of the detector units 513, 530, 542 may be mounted to the waistband of the same nappy (e.g., nappy 1600). A separate non-elastic link 460, 576, 585 connects each optical fibre of the respective detector units 513, 530, 542 to the respective detector unit attachment points 701, 715, 725. Each detector unit attachment point 701, 715, 725 is fixedly attached to the external surface 1590 of the nappy 1600, preferably near to the waistband of the nappy 1600. As mentioned, each detector unit attachment point 701, 715, 725 forms part of a respective expandable member (only the detector unit attachment points 701, 715, 725 of the expandable members are shown in FIG. 13). Each expandable member may be fixedly attached to the external surface 1590 of the nappy 1600 at a different location. For example, a first expandable member may be located on the front 1530 of the nappy 1600, a second expandable member may be located on the crotch region 1540 of the nappy 1600, and a third expandable member may be located on the back 1570 of the nappy 1600. In FIG. 13, only optical detectors are shown. However, any suitable type of detector unit may be used. Advantageously, using more than one sensing device results in higher signal generation and higher sensitivity to the nappy expansion. Using multiple sensing devices where separate expandable members are fixedly attached to different locations on the external surface 1590 of the nappy 1600 improves accuracy of the indication of the fullness of the nappy 1600. Furthermore, the displacements measured by the plurality of sensing devices may be used to determine whether the nappy 1600 has been filled by liquids (e.g. urine) or solids (e.g. feces). FIG. 13 relates to examples where the sensing device is attached to the external surface of the nappy after the nappy has been manufactured, and examples where the expandable member of the sensing device is integrated onto the external surface of the nappy during manufacture.

Figure 14:
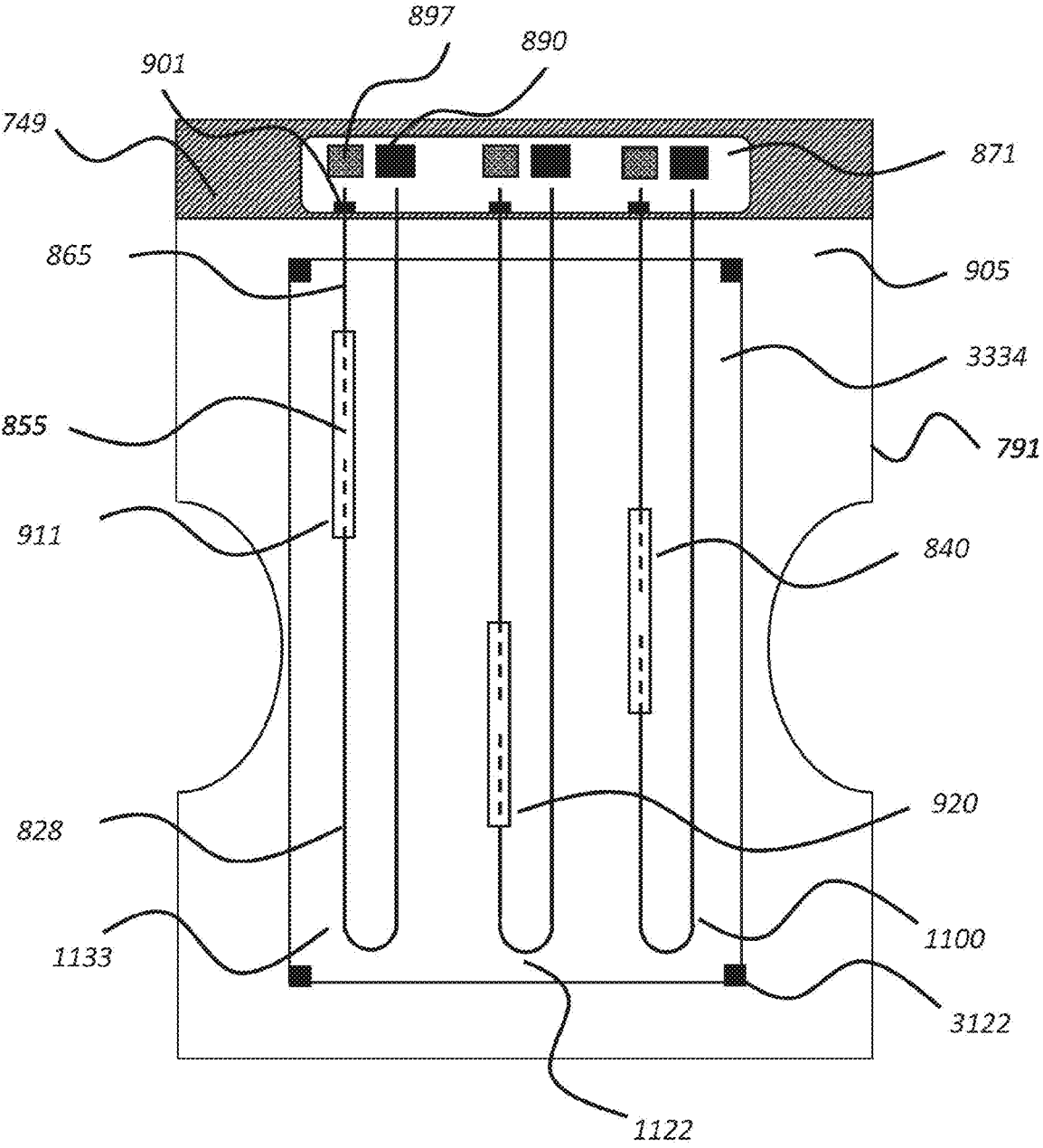
FIG. 14 is a plan view of an alternative exemplary sensing device attached to the external surface of a nappy, the sensing device comprises three sensor elements.
Figure 15:
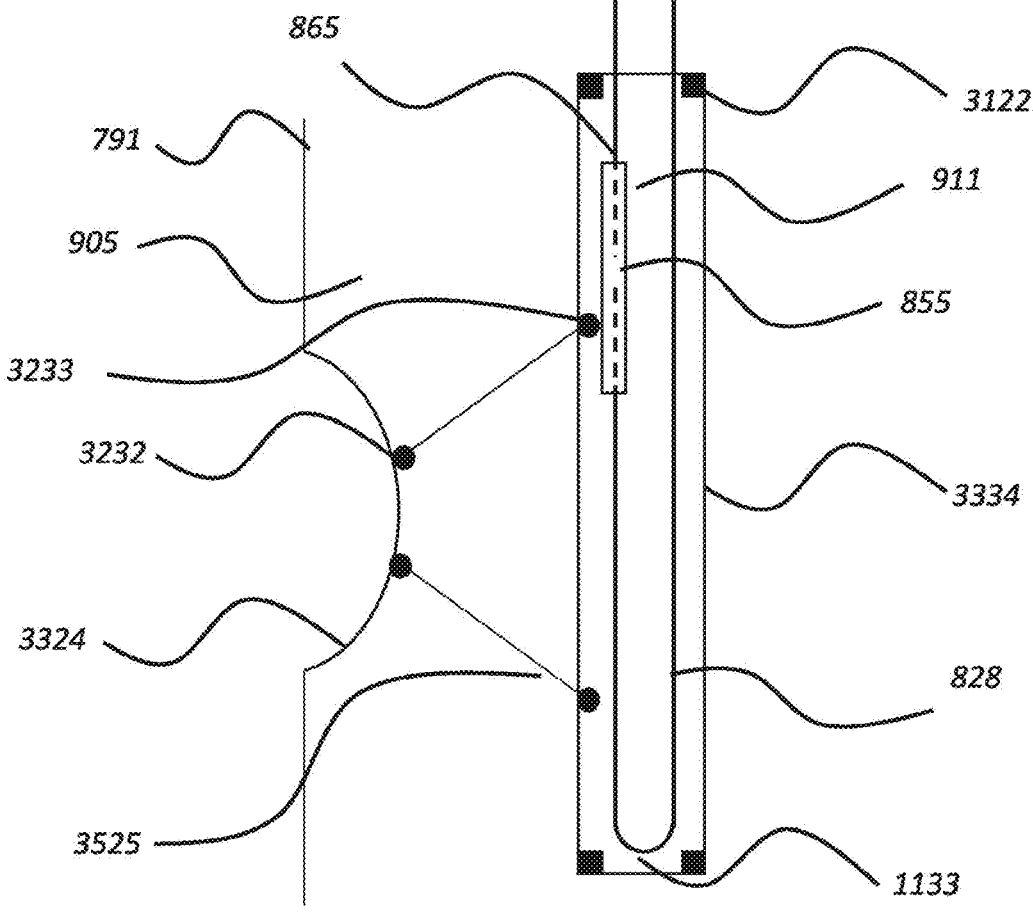
FIG. 15 is a partial plan view of the arrangement of FIG. 14, showing additional features of the exemplary sensing device of FIG. 14.

FIGS. 14 and 15 show plan views of an alternative example of a sensing device attached to the external surface 905 of a nappy 791. As seen in FIG. 14, the nappy 791 has the same configuration as nappy 1600—a front, a crotch region between elasticated edges of the nappy, and a back. The front of the nappy 791 is connected to a waistband section 749. Alternatively, the back of the nappy may be connected to the waistband section 749. The sensing device comprises a detector unit 871 and three sensor elements 1100, 1122, 1133, but a different number of sensor elements (e.g. one or more) could be used if desired. The detector unit 871 is mounted on the waistband section. In alternative examples, the detector unit 871 may be mounted at another suitable position on the external surface 905 of the nappy 791. For example, on the front of the nappy 791, near the waistband section 749. The detector unit 871 comprises three light sources and three light detectors. Each light source/detector pair is linked to one of the three sensor elements 1100, 1122, 1133.

The sensing device also comprises one or more expandable members 3334 fixedly attached to the external surface 905 of the nappy 791 by attachment points 3122. In FIG. 14, the expandable member 3334 includes one elastic element (similar to the elastic patch of FIG. 1) that is configured to stretch as the nappy 791 expands. The expandable member 3334 is fixedly attached (e.g., by glue or Velcro etc.) to the external surface 905 of the nappy 791 by attachment points 3122 positioned at each corner of the elastic patch. The expandable member 3334 covers a substantial area of the external surface 905 of the nappy 791. As an alternative to an elastic patch, the expandable member 3334 may be a flexible polymeric substrate.

Each sensor element 1100, 1122, 1133 is positioned on the elastic element of the expandable member 3334. Whilst FIG. 14 shows the sensor elements 1100, 1122, 1133 positioned on one elastic patch, any suitable number of elastic elements may be used. For example, each sensor element 1100, 1122, 1133 may be positioned on their own expandable member 3334 (e.g. FIG. 15 shows a single sensor element 1133 on its own elastic element 3344).

The sensor elements 1100, 1122, 1133 and expandable member 3334 may be manufactured together as a disposable patch configured to be laid on the external surface 905 of the nappy 791 before the nappy 791 is used. Considering the sensor element 1133 in more detail, the detector unit 871 comprises a light source 897 (such as a light-emitting diode) and light detector 890 (such as a photodetector) associated with the sensor element 1133. The sensor element 1133 comprises two optical fibres 865, 828 and a micro tube 911 extending between the two optical fibres 865, 828. The micro tube 911 may be metal or plastic. A first end of the first optical fibre 865 is positioned in front of the light source 897, and is fixed to the detector unit 871 by an attachment point 901. The first optical fibre 865 extends across part of the external surface 905 of the nappy 791. For example, in FIG. 14, the first optical fibre 865 extends across the front of the nappy 791. A second end of the first optical fibre 865 extends partially into a first end of the micro tube 911. In FIG. 14, the micro tube 911 is positioned on the front of the nappy 791. A first end of the second optical fibre 828 is positioned in front of the light detector 890 in the detector unit 871. The first end of the second optical fibre 828 is not fixed to the detector unit 891 and is therefore free to move towards and away from the light detector 890. There is a first gap between the light detector 890 and the first end of the second optical fibre 828. The second optical fibre 828 extends across a substantial length of the external surface 905 of the nappy 791. For example, in FIG. 14, the optical fibre 828 extends across the front, the crotch region, and the back of the nappy 791, and then folds back on itself toward the micro tube 911. A second end of the second optical fibre 828 extends partially into a second end of the micro tube 911, such that two optical fibres 865, 828 are substantially coaxial within the micro tube 911. There is a second gap 855 between the second ends of the two optical fibres 865, 828 inside the micro tube 911. Sensor elements 1100 and 1122 are configured in an analogous manner to sensor element 1133, with their respective micro tubes 840 and 920 disposed at different locations with respect to the nappy 791.

The optical fibres 828, 865 of the sensor element 1133 are attached to the expandable member 3334 such that the optical fibres 828, 865 can freely move, to allow for expansion of the nappy 791. For example, the optical fibres 828, 865 may be attached (e.g. glued) to the expandable member 3334 only in specific places, such that the optical fibres 828, 865 can freely move, particularly inside the micro tube 911, as the nappy 791 expands. In other examples, the optical fibres 828, 865 may partially or fully be contained within one or more sheaths. The sheaths are attached to the expandable member 3334 by any suitable attachment mechanism (e.g., adhesive). Containing the optical fibres 828, 865 within the sheaths still allows the optical fibres 828, 865 to move apart from each other in the micro tube 911 as the nappy 791 expands.

As shown in FIG. 15, the expandable member further comprises two elastomeric polymers 3525 attached between attachment points 3233 on the elastic patch 3334 and attachment points 3233 on the elasticated edge 3324 of the nappy 791. Elasticated edge 3324 of nappy 791 are equivalent to the elasticated edge 1560 of nappy 1600 described previously. The elastomer polymers 3525 provide sensitivity when detecting expansion of the expandable member 3334.

In use, the sensor element 1133 is configured to provide a sensor signal to the detector unit 871, where the sensor signal varies in dependence on an amount of stretching of the elastic element. The additional sensor elements 1100, 1122 are also configured to provide respective sensor signals to the detector unit 871, wherein each sensor signal varies in dependence on the amount of stretching of the elastic element. For example, the detector unit 871 is configured such that a relative displacement between the two optical fibres 865, 828 (this is caused by the elastic element stretching) results in a change in the amount of light reaching the light detector 890, thereby producing a change in an output signal from the light detector 890. In the unexpanded state, the first gap (near the light detector 890) and the second gap 855 (in the micro tube 911) each have a predetermined size, and the detected signal has a predetermined value. As the external surface 905 of the nappy 791 expands (due to urine and/or feces ingress inside the nappy 791) and the elastic element stretches, the second gap 855 in the micro tube 911 increases. The nappy expansion may also cause the second end of the optical fibre 828 to move further away from the light detector 890, thereby increasing the first gap. These gap increases cause a drop in the signal at the light detector 890 (the detected signal is proportional to gap increase, and therefore the volume of urine and/or feces inside the nappy), thereby indicating that the nappy 791 has expanded. Advantageously, the combination of the first gap and the second gap 855 changing results in a higher sensitivity to the nappy expansion.

The increase in the gap(s) will only be a few mm, but the overall distance change in the external surface 905 of the nappy 791 (from the nappy's original position) when urine and/or feces ingress inside the nappy 791, can be several cm. To accommodate this large change, a plurality of sensor elements are used, as shown in FIG. 14. The three sensor elements 1100, 1122, 1133 are spaced across the external surface 905 of the nappy 791. For example, the micro tube 911 is located at the front of the nappy 791, a second micro tube 840 is located in the crotch region of the nappy 791, and a third micro tube 920 is located towards the back of the nappy 791. Positioning the micro tubes at different locations on the nappy 791 increases the accuracy of expansion detected. For example, the micro tube 840 located in the crotch region of the nappy 791 will be likely be the first to detect an expansion as the nappy 791 fills with urine and/or feces, due to its positioning at the wearer's groin region. Furthermore, the varying locations are advantageous for when the wearer is in different positions, for example lying down vs. standing up, as different parts of the nappy 791 will expand first depending on the position of the wearer.

Conductive Detectors

Figure 16:
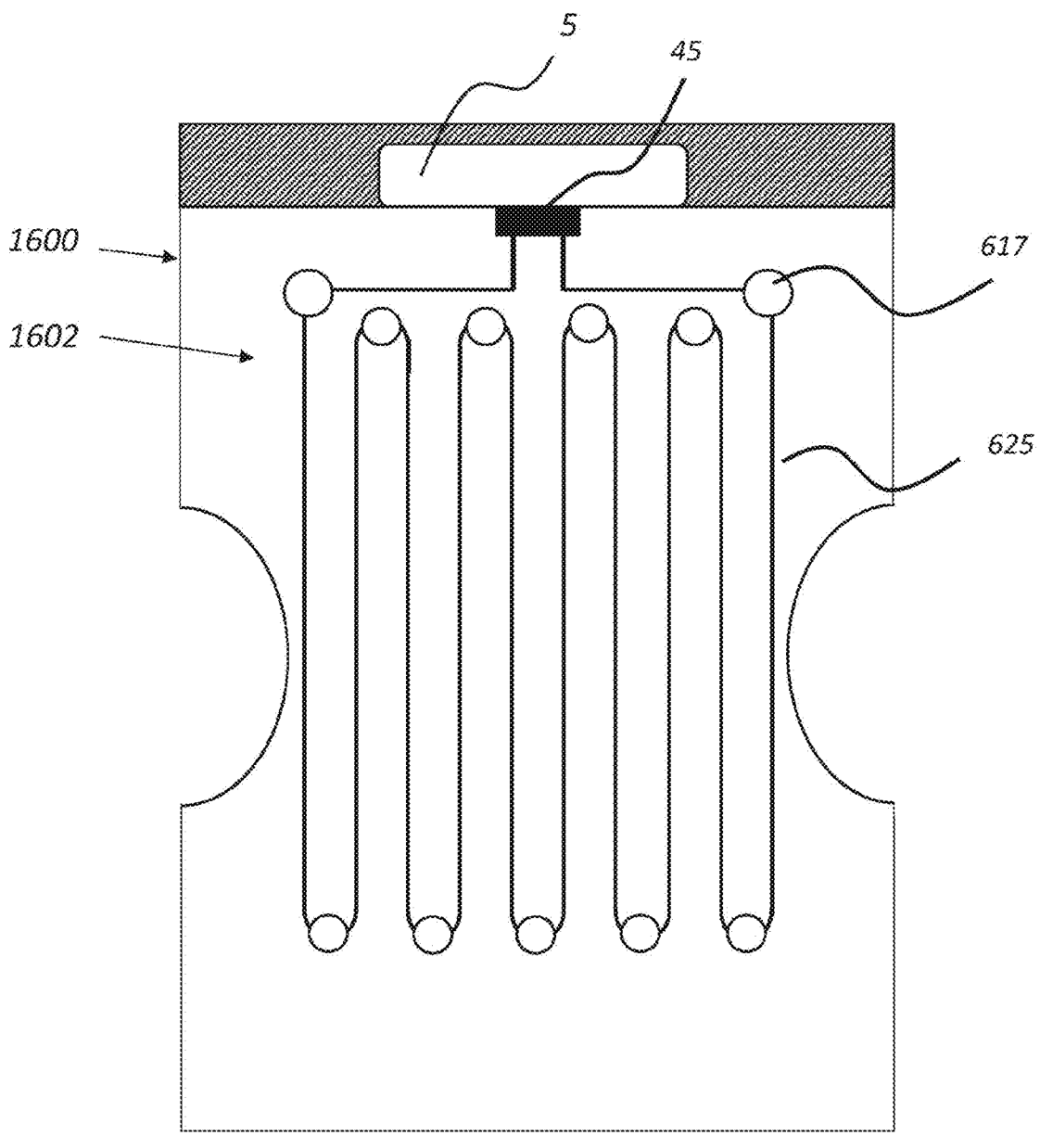
FIG. 16 is a plan view of an alternative exemplary sensing device attached to the external surface of a nappy.
Figure 17:
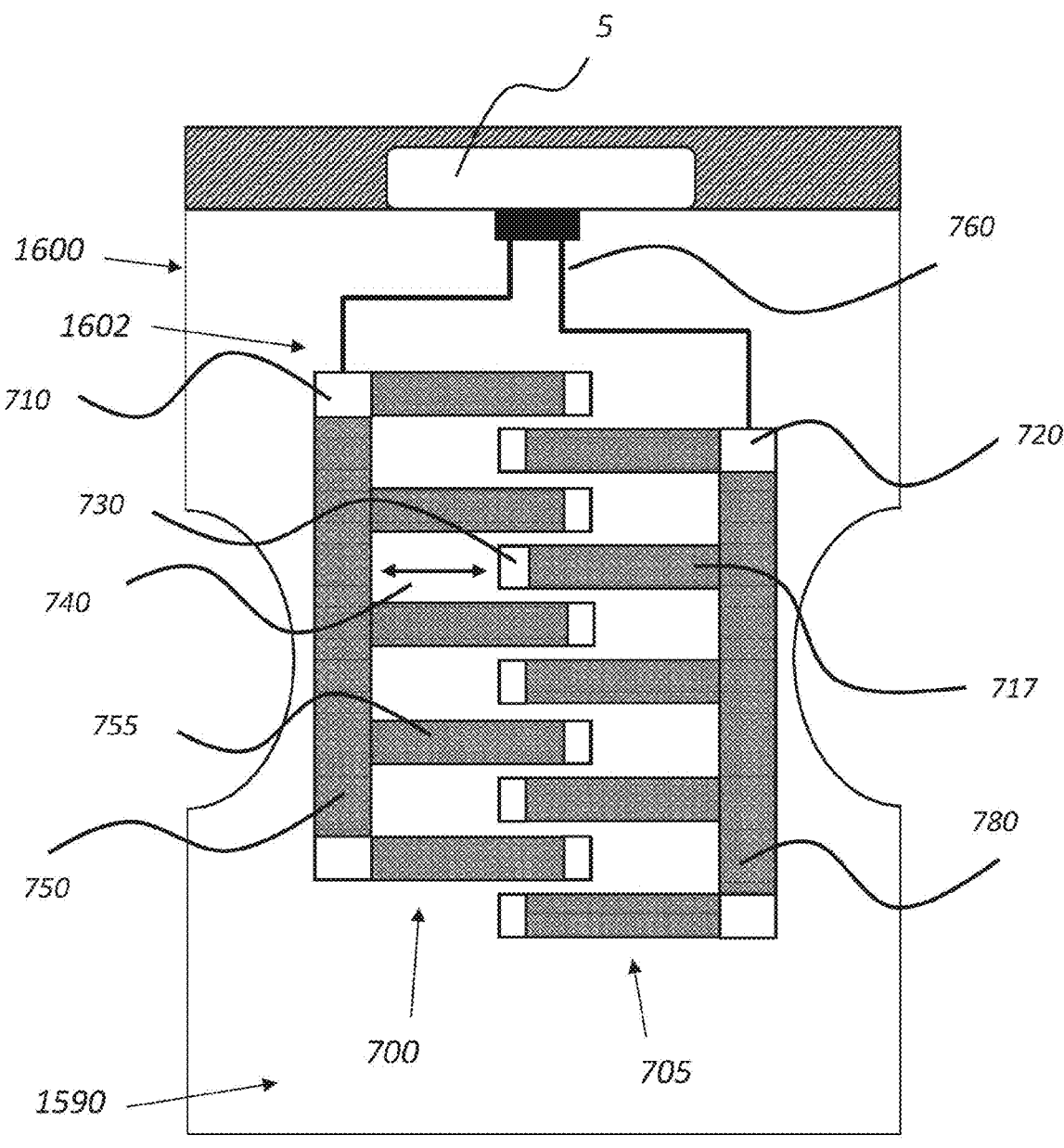
FIG. 17 is a plan view of an alternative exemplary sensing device attached to the external surface of a nappy.

FIGS. 16 and 17 show alternative examples of a sensing device on the external surface of a nappy 1600. The nappy 1600 is equivalent to nappies 1600, 1 and 791 above. In these examples, the detector unit comprises a resistive or capacitive detector, and the elastic elements are conductive. For example, the elastic elements may be made from conductive polymers. The detector unit is configured to detect expansion of the expandable member by detecting a change in length of at least one of the elastic elements. For example, as the nappy expands, the elastic elements will stretch, thereby changing in length (as in the case of a resistor). The change in length of the elastic elements causes a change in the signal detected in the detector unit, indicating an expansion of the expandable member.

In the example shown in FIG. 16, the sensing device comprises a detector unit 5 directly coupled to an expandable member 1602 by a detector unit attachment point 45. The detector unit attachment point 45 may be equivalent to the detector unit attachment point 45 previously described. The expandable member 1602 comprises one or more elastic elements 625 extending between multiple attachment points 617, 45. The attachment points 617 are connected via the elastic elements 625 so as to form a meandering pattern. The attachment points 617 are positioned at each turn of the meandering pattern. In FIG. 16, the detector unit 5 is mounted on a waistband section of the nappy 1600. However, in some examples, the detector unit 5 may be positioned in an alternative position on the nappy 1600, such as below the waistband section. The detector unit attachment point 45 is positioned centrally on the front of the nappy 1600, next to the detector unit 5. The other attachment points 617 comprise six front attachment points disposed approximately linearly and transversely across the front of the nappy 1600, and five back attachment points disposed approximately linearly and transversely across the back of the nappy 1600. The six front attachment points are fixedly attached to the external front surface of the nappy 1600 near to a front upper edge of the nappy (i.e., near to the waistband). The five back attachment points are fixedly attached to the external back surface of the nappy 1600 near to a back upper edge of the nappy (i.e., near to the back waistband). Two of the elastic elements 625 extend from the central detector unit attachment point 45 transversely across the front of the nappy 1600 in opposite directions towards the two outer front attachment points 617. The remaining elastic elements 625 extend substantially longitudinally (lengthways) in a meandering pattern over the external surface of the nappy 1600. In particular, two further elastic elements 625 extend longitudinally (lengthways), from each of the two outer front attachment points 617 down the front, crotch region and up the back of the nappy 1600 to reach the two outer back attachment points 617. The elastic elements 625 then connect to the remaining attachment points 617 in a meandering configuration between the front attachment points and the back attachment points, with an attachment point at each turn. The elastic elements 625 are free to stretch between the attachment points 617, 45 as the nappy 1600 expands. The elastic elements 625 are thinner than the elastic elements of FIGS. 1-7, so as to allow the elastic elements 625 to meander more easily. For example, in FIG.

16, the elastic elements 625 may be made from thin strips or threads or wires of conductive elastic material. FIG. 16 includes both examples where the sensing device is attached to the external surface of the nappy after the nappy has been manufactured, and examples where the expandable member of the sensing device is integrated onto the external surface of the nappy during manufacture.

Figure 18:
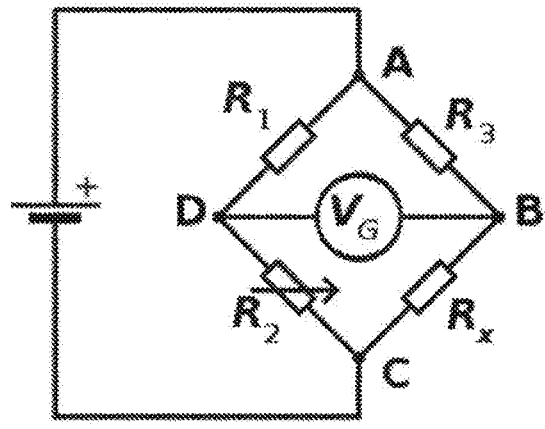
FIG. 18 is a circuit diagram of a Wheatstone bridge for measuring resistance, and for use with the exemplary sensing device of FIG. 16.

In use, the detector unit 5 is configured to detect expansion of the expandable member 1602 by detecting a change in resistance of the expandable member 1602 due to the change in length. As the elastic elements 625 are constructed of a conducting material, the elastic elements 625 have a resistance R given by:

$$R = \frac{\rho L}{A} \tag{2}$$

where ρ is the resistivity of the conductive elastic elements 625, L is the total path length of the elastic elements 625, and A is the cross-sectional area of the elastic elements 625. As the elastic elements 625 are stretched (due to expansion of the nappy 1600), the path length L increases, thereby increasing the resistance R through the conductive elastic elements 625. The change in resistance can be detected in the detector unit 5 using a standard Wheatstone bridge circuit. The change in resistance R of the elastic elements 625 is a direct consequence of the volume increase in the nappy 1600. In other words, the resistance varies with the volume of urine and/or feces inside the nappy 1600. A standard Wheatstone bridge circuit is shown in FIG. 18. Rx in the Wheatstone bridge circuit is the unknown resistance of the expanded elastic elements 625.

In an alternative example, as shown in FIG. 17, the elastic elements are conductive and act as electrodes, such that the sensing device forms a variable capacitor. For example, the elastic elements may be made from conductive polymers, and may be up to 0.3 mm thick. In FIG. 17, the sensing device comprises a detector unit 5 directly coupled to an expandable member 1602 by a detector unit attachment point 45. The detector unit attachment point 45 may be equivalent to the detector unit attachment point 45 previously described. The expandable member 1602 comprises multiple elastic elements extending between multiple attachment points. The attachment points comprise a first set of attachment points 710 connected via one or more first elastic elements so as to form a first digitated pattern 700. The one or more first elastic elements form a first set of the one or more first elastic elements. The attachment points also comprise a second set of attachment points 720 connected via one or more second elastic elements so as to form a second digitated pattern 705. The one or more second elastic elements form a first set of the one or more second elastic elements. The first and second digitated patterns 700, 705 are arranged in an interdigitated pattern. In more detail, the first digitated pattern 700 comprises a longitudinal elastic element 750 fixedly attached to the front of the nappy 1600 at one end, by one attachment point 710 of the first set of attachment points, and fixedly attached to the back of the nappy 1600 at the other end, by another attachment point 710 of the first set of attachment points. First ends of several transverse elastic elements 755 are connected to the longitudinal elastic element 750. Each transverse elastic element 755 is also fixedly attached to a respective attachment point at its other end. Thus, the transverse elastic elements 755 effectively form the digits of the first digitated pattern 700.

The digits extend towards a centreline of the nappy 1600. The second digitated pattern 705 is a mirror image of the first digitated pattern 700, but shifted out of line with the first digitated pattern 700, such that the transverse elastic elements 755, 717 of each digitated pattern 700, 705 are staggered. The second digitated pattern 705 comprises a longitudinal elastic element 780 fixedly attached to the front of the nappy 1600 at one end, by one attachment point 720 of the second set of attachment points, and fixedly attached to the back of the nappy 1600 at the other end, by another attachment point 720 of the second set of attachment points. First ends of several transverse elastic elements 717 are connected to the longitudinal elastic element 780. Each transverse elastic element 717 is also fixedly attached to a respective attachment point 730 at its other end. Thus, the transverse elastic elements 717 effectively form the digits of the second digitated pattern 705. The digits extend towards the centreline of the nappy 1600. As mentioned above, the first and second digitated patterns 700, 705 interlink to form the interdigitated pattern. The transverse elastic elements 755, 717 may have lengths covering a substantial portion along the width of the nappy 1600 (i.e., each extending between the elasticated edges 1560 of the nappy 1600 and beyond the centreline of the nappy 1600). The two longitudinal elastic elements 750, 780 have lengths covering a substantial portion along the length of the nappy 1600. For example, the two longitudinal elastic elements 750, 780 cover a substantial length of the front, crotch region and back of the nappy 1600. The two longitudinal elastic elements 750, 780 are connected to the detector unit 5 by conductive links 766 between the detector unit attachment point 45, and at least one of the attachment points 710 of the first pattern 700 and at least one of the attachment points 720 of the second pattern 705.

The first and second patterns 700, 705 are separated by gaps (e.g., gap 740) between the longitudinal elastic elements of one pattern and the distal ends of the transverse elastic element of the other pattern. For example, as shown in FIG. 17, there is a gap 740 between the longitudinal elastic element 750 of the first pattern 700 and an attachment point 730 on the distal end of one of the transverse elastic elements 717 of the second pattern 705. There are also vertical gaps between the distal ends of each of the transverse elastic elements (e.g., there is a gap between the top transverse elastic element of the first pattern and the top transverse elastic element of the second pattern in FIG. 17). FIG. 17 includes both examples where the sensing device is attached to the external surface of the nappy after the nappy has been manufactured, and examples where the expandable member of the sensing device is integrated onto the external surface of the nappy during manufacture.

In use, the detector unit 5 is configured to detect expansion of the expandable member 1602 by detector a change in capacitance due to the change in length of the at least one elastic elements 750, 755, 780, 717. For example, as the nappy 1600 expands, the elastic elements 750, 755, 780, 717 change in length as they stretch with the nappy 1600. The change in length of the elastic elements 750, 755, 780, 717 causes a change in the gap 740 size, thereby causing a change in capacitance. The change in capacitance indicates that the nappy 1600 has expanded. In other words, the nappy expansion causes a change in size of the gap 740. This change in gap 740 changes the interdigitation of the first and second patterns 700, 705. Thus, the detector unit 5 is configured to detect expansion of the expandable member 1602 by detecting a change in capacitance due to a change in interdigitation of the first and second patterns 700, 704.

Figure 19:
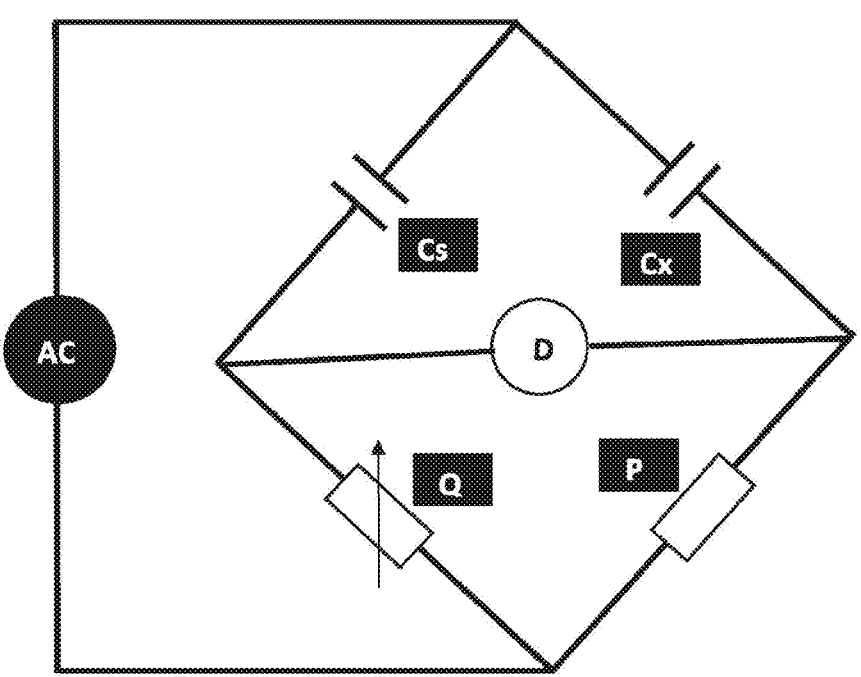
FIG. 19 is a circuit diagram of a capacitance bridge for measuring capacitance, and for use with the exemplary sensing device of FIG. 17.

For example, as the nappy 1600 expands, the first and second digitated patterns 700, 705 move apart from each other, changing the amount of interdigitation between the patterns 700, 705. The change in capacitance is detected using a capacitance bridge in the detector unit 5. FIG. 19 shows a standard capacitance bridge circuit. Cs is a precise standard capacitor, Cx is the unknown capacitance, provided by the expanding elastic elements 750, 755, 780, 717 attached to the nappy 1600. As urine and/or feces ingresses the nappy 1600, the volume of the nappy 1600 expands and the capacitance changes. Q and P are standard resistors, one or both of which are adjustable. An AC supply is used, and the null detector D must be an AC instrument. A low-current rectifier ammeter may be used as a null detector. Q is adjusted until the null detector indicates zero. When this is obtained the capacitor bridge is balanced. The capacitance Cx change indicates the volume of urine and/or feces inside the nappy 1600. The change in capacitance is proportional to the volume change, i.e., the amount of urine and/or feces inside the nappy 1600.

Body Movement

Movement of a nappy wearer's body (for example, getting up, walking around, and lying down) may affect the sensing capabilities of the sensing device. The body movement may cause changes to the detected signal, thereby leading to inaccurate expansion measurements. A MEMS (micro electro mechanical system) capacitor-based gyroscope or an accelerometer may be used in the detector unit to record any movement in the body of the nappy wearer. Appropriate corrections may then be applied electronically and/or in the software to differentiate between the actual signal (due to urine and/or feces ingress and consequent volume expansion) and any signal changes caused by the body movement.

Figure 23A:
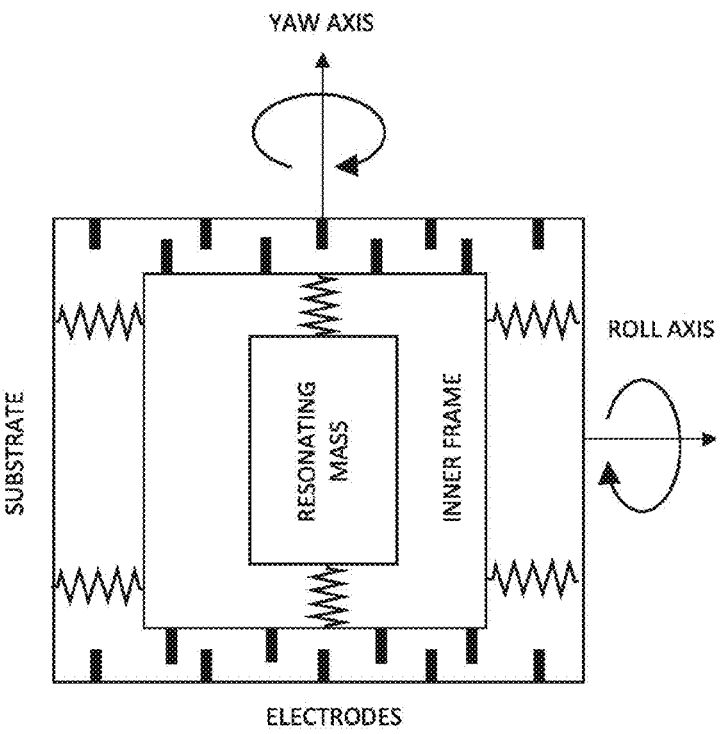
FIG. 23*a* is a circuit diagram of a gyroscope for measuring movement, and for use with any exemplary sensing device.

A MEMS gyroscope is shown in FIG. 23*a*. The MEMS gyroscope is constructed such that the inner frame containing the resonating mass is connected to the substrate by springs at 90 degrees relative to the resonating motion. The Coriolis acceleration is measured through capacitance sensing on the electrodes mounted between the inner frame and the substrate. Gyroscopes measure angular velocity (specified in mV/deg/sec).

Figure 23B:
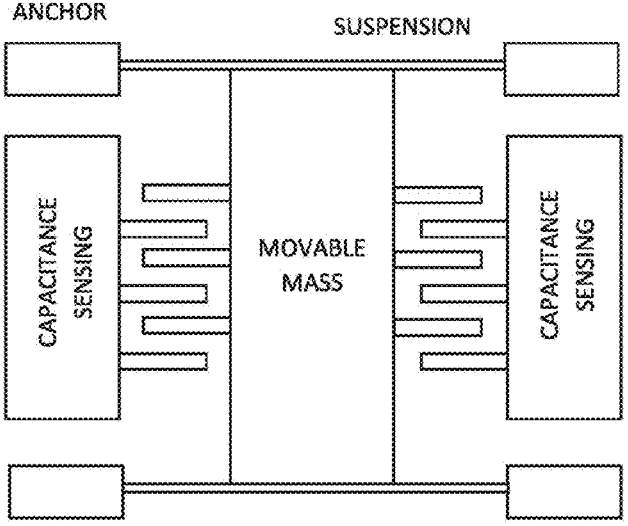
FIG. 23*b* is a circuit diagram of an accelerometer for measuring movement, and for use with any exemplary sensing device.

A MEMS accelerometer is shown in FIG. 23*b*. This is a simple one-axis accelerometer. If more sets of capacitors are kept at 90 degrees to each other, 2 or 3-axis accelerometers can be produced. The movable plates and the fixed outer plates act as the capacitor plates. When acceleration is applied, the proof mass moves accordingly. This produces a capacitance between the movable and the fixed outer plates. When acceleration is applied (due to body movement), distance between the two plates change, and the capacitance changes. Accelerometers measure linear acceleration (specified in mV/g) along one or several axes.

Power Supply

Figure 20:
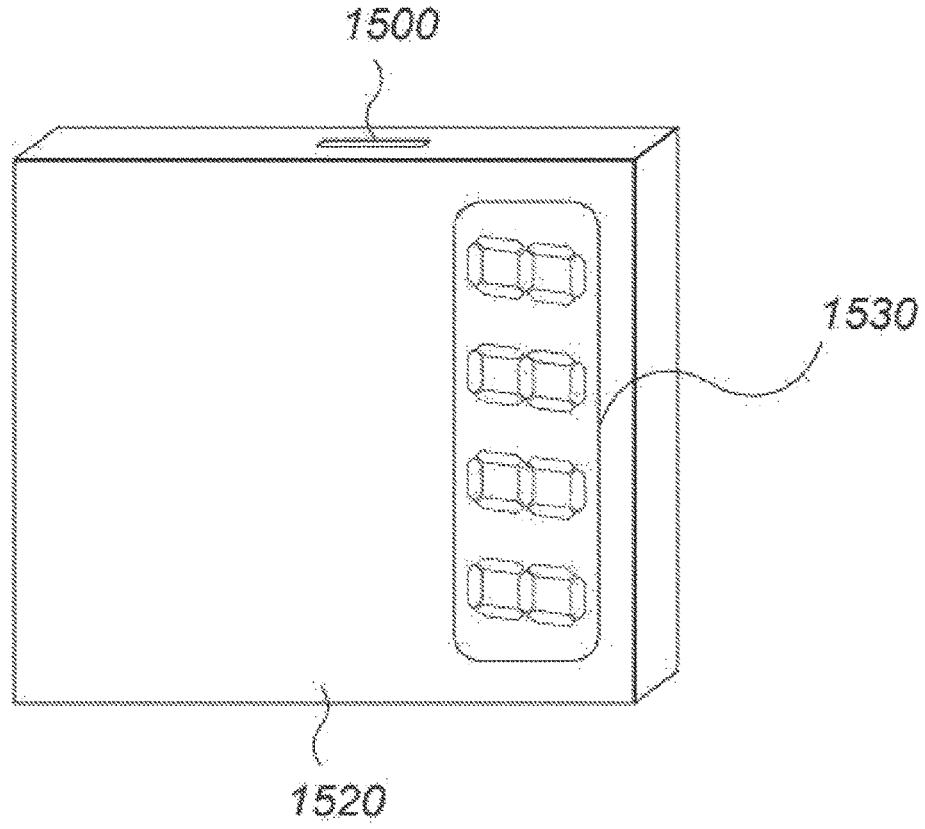
FIG. 20 is a perspective view of an exemplary electronic control and power supply unit for powering any exemplary sensing device.

FIG. 20 schematically illustrates an electronic control and power supply unit 1520 that may be used with any example of the sensing device described above. The control and power supply unit 1520 may house the detector unit described above. The control and power supply unit 1520 may comprise signal amplifiers, an analogue-to-digital converter, a microcontroller or other processor, memory, a data logger, a wireless transmission system (e.g. Bluetooth™), discrete or integrated electronic components, FPGAs, DSPs, ASICs, etc. The electronic control and power supply may have a digital display 1530 which is configured to display instantaneous volume readings. The electronic control and power supply unit 1520 may also comprise an audio indicator, e.g. for signalling an alert if the volume of the urine and/or feces inside the nappy is outside a target range. The entire electronic control and power supply may be contained within a housing of the unit 1520.

Measurements determined by the sensing device can be captured at intervals and stored in the data logger prior to processing in the microprocessor. Measurements may be taken and recorded in the data logger as frequently as desired—e.g. every minute or every hour. Data from the data logger or the microprocessor may be transmitted by the transmission system to a remote device or server. This may be a smartphone, laptop, pager or other device. The remote device can keep a record of liquid volume data that can be used for clinical evaluation. This data logging may be used by clinicians to monitor the level of incontinence in a patient.

The electronic control and power supply unit 1520 may further comprise a rechargeable coin cell for supplying electrical power to the sensing device and the electrical components of the electronic control and power supply unit 1520. The electronic control and power supply unit 1520 supplies a voltage of 5V or less. The electronic control and power supply unit 1520 further comprises a USB port 1500 by which data may be retrieved from the data logger.

The electronic control and power supply unit 1520 may be attached to a nappy via adhesive pads, a hook-and-loop connecting mechanism or similar, or it may be integrated into a housing or casing of the sensing device. Alternatively, the electronic control and power supply unit 1520 may be communicatively coupled to the sensing device. For example, the electronic control and power supply unit 1520 may be connected by a cable, or other suitable wired or wireless power and communication link, and be located remotely from the sensing device—e.g. in a pocket of clothing worn by the wearer, or on a bedside trolley.

Analytics

Using the sensing device of any of the previously described examples, the detected signal may be used to generate volume vs. time data. From this data, nappy fullness parameters, such as a) the volume of urine and/or feces, b) flow rate of the urine, and c) frequency of the discharge, may be calculated using an analytical method, e.g. a definite integral. This is very useful for incontinence assessment. For example, the volume of urine inside the nappy may be calculated using an empirical method. Multiple experiments are performed on a range of nappies of different sizes and absorption capacities. Known quantities of liquid (e.g., saline water) are injected into the nappy and the output signal at the light detector (e.g., light detector 140) is recorded. The quantity of liquid may be up to several litres. Software is used to convert the output signal into the amount of liquid inside the nappy. The result is displayed as a volume. The output signal (mV) is converted into a volume (ml) of liquid (using the empirical method stated above), volume vs time data s collected, and a volume vs time graph may be generated. Using a definite integral, the volume of urine discharged by the wearer in any given time period can be deduced from the area under the curve. The flow rate (dm l/dt) of the discharge can also be determined at any instance during the use of the nappy. This is particularly useful for incontinence assessment of a patient, which is currently done manually.

Figure 21:
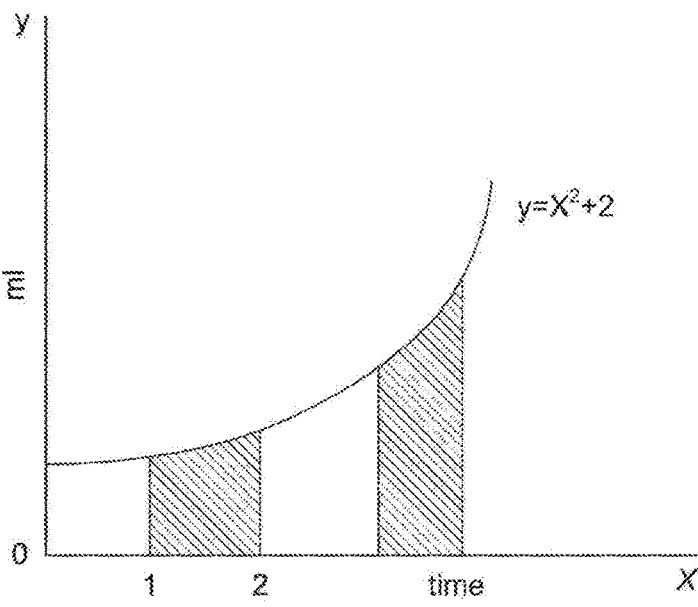
FIG. 21 is an exemplary graph of volume vs time data for determining nappy fullness parameters.

FIG. 21 is an exemplary graph of volume (ml) against time used to illustrate how the volume of liquid, flow rate, and frequency of discharge inside the nappy may be computed. This can be correlated to experimental findings. A software algorithm can be used to determine the parameters and the results can be displayed digitally. The volume V of urine/feces discharged by the user in a given time period for the graph shown in FIG. 21 may be computed using the definite integral:

$$V = \pi \int y^2 dx \qquad (3)$$

where y is an exemplary function y=x²+2 in FIG. 21, and x is time. In general, the equation of the curve y=f(x) can be generated from the recorded data using software. The flow rate is computed as dml/dt and the frequency computed from the number of events over a period of time.

Due to the ingress of urine and/or feces, the expanding nappy applies a pressure on the elastic elements. This pressure can be computed as:

$$P = \frac{F}{A} \qquad (4)$$

where P is the pressure on the elastic elements, F is the force on the elastic elements and A is the total area of the elastic elements. The force F can be detected using a force detector. Using the empirical method described above, the pressure P can be related to the volume of the liquid inside the nappy. The empirical method involves the injection of a known quantity of liquid (up to several litres) inside the nappy. This provides an alternative method of detecting the volume inside the nappy at any given instance, during use. An appropriate software may be compiled based on this method to generate and display a digital value of the volume of the urine and/or feces inside the nappy.

A filtering algorithm may be used to avoid false detections caused by movement of the wearer. For example, time sampling may be used to remove unwanted signals due to movement by wearer. The sensing device is configured to process the output signal from the detector unit so as to remove transient features caused by movement of the wearer, for example when walking around, or turning in bed. Sensor data may be logged over time and processed to determine the frequency, flow rate, and/or volume of the wearer's urination.

The sensing device may also comprise an output device for providing an indication of fullness of the nappy, such as a speaker, a display, or a light-emitting component (e.g. an LED). The output device may comprise electronic circuitry, such as a radio transmitter, configured to transmit a signal, e.g. to a smartphone e.g. of a parent, guardian or carer. The indication may be binary (e.g. full or not full), or may indicate a degree of fullness of the nappy.

The sensing device may be configured to determine when the detected displacement in the nappy exceeds a predetermined threshold. The output device may be configured to provide an indication, e.g. transmit a signal, in response to determining that the detected displacement exceeds the predetermined threshold. In this way, the sensing device may be used to provide an alert to a parent, guardian or carer that a nappy, e.g. worn by a baby, infant, toddler, child, adult or animal, has been filled, e.g. by urine or feces, and needs to be replaced.

A first expansion of the expandable member is measured before or soon after the nappy has been put on, or is preconfigured. This first expansion is representative of the state or stretch in the nappy 1600 when the nappy 1600 is in an unsoiled 'empty' state, i.e., the unexpanded state. Over time, the sensing device records, at intervals, further measurements of the expansion. Each further measurement of expansion can be compared with the first expansion measurement. If the sensing device records an expansion measurement that is greater than the first expansion measurement by a predetermined threshold, indicating a significant expansion of the nappy, the sensing device determines that the nappy is filling up or has been filled, e.g. by urine and/or feces. Consequently, the sensing device may be arranged to issue an alert to the parent or carer that the nappy has been soiled and therefore requires changing—e.g. by sending a radio message to a baby monitor device, or to an app on a phone belonging to the parent or carer. In some examples, more complex processing of the expansion measurement may be performed, e.g. to filter out changes arising due to movement of the wearer.

The invention claimed is:

1. A sensing device for attaching to an external surface of a nappy, the sensing device comprising:
   an expandable member comprising one or more elastic elements extending between a plurality of attachment points, wherein the attachment points are configured to fixedly attach the expandable member to the external surface of the nappy, and wherein the one or more elastic elements are configured to stretch as the attachment points move apart such that the expandable member is configured to expand in accordance with expansion of the nappy; and
   a detector unit coupled to the expandable member, wherein the detector unit is configured to detect expansion of the expandable member, and is further configured to determine a nappy fullness parameter based on the detected expansion of the expandable member.

2. The sensing device of claim 1, wherein the expandable member is sized and shaped to cover a substantial area of the external surface of the nappy, with at least some of the attachment points configured to be disposed on or near to edges of the nappy.

3. The sensing device of claim 2, wherein the expandable member is sized and shaped to extend across a full width of a crotch region of the nappy.

4. The sensing device of claim 1, wherein the detector unit comprises one of: an optical detector, a resistive detector, or a capacitive detector.

5. The sensing device of claim 1, wherein the one or more elastic elements comprise multiple elastic elements arranged in a polygon with the attachment points at one or more corners of the polygon.

6. The sensing device of claim 5, wherein the expandable member further comprises one or more transverse elastic elements extending between the multiple elastic elements, wherein the one or more transverse elastic elements are concentrated within a specified area of the polygon.

7. The sensing device of claim 1, wherein the one or more elastic elements comprise one of an elastic patch or an elastic net, and wherein the attachment points comprise attachment points at a periphery of the one of an elastic patch or an elastic net.

8. The sensing device of claim 1, wherein the detector unit is configured to detect expansion of the expandable member by detecting a relative displacement between the attachment points.

9. The sensing device of claim 1, wherein the attachment points comprise a detector unit attachment point directly coupled to the detector unit, wherein:

(i) the detector unit is configured to detect expansion of the expandable member by detecting a relative displacement between the detector unit attachment point and at least one other attachment point;

(ii) the relative displacement between the detector unit attachment point and the at least one other attachment point is configured to cause the expandable member to pull the detector unit attachment point in a direction away from the detector unit;

(iii) the detector unit comprises a light source and a light detector, and wherein the detector unit is configured such that an amount of light reaching the light detector from the light source varies in dependence on the relative displacement between the detector unit attachment point and the at least one other attachment point, thereby producing a change in an output signal from the light detector;

(iv) the attachment points further comprise: a first attachment point connected to the detector unit attachment point via a longitudinal elastic element; and one or more secondary attachment points connected to the longitudinal elastic element via one or more transverse elastic elements; and (v) a central junction point is connected to the detector unit attachment point via a central elastic element; and wherein the attachment points further comprise multiple attachment points spaced around the central junction point, the multiple attachment points connected to the central junction point via respective radial elastic elements.

10. The sensing device of claim 1, wherein the one or more elastic elements are conductive, and wherein the detector unit is configured to detect expansion of the expandable member by detecting a change in length of at least one of the one or more elastic elements, further wherein the detector unit is configured to detect expansion of the expandable member by detecting a change in resistance of the expandable member due to the change in length.

11. The sensing device of claim 10, wherein the detector unit is configured to detect expansion of the expandable member by detecting a change in capacitance due to the change in length of the at least one elastic element, wherein:

(i) the attachment points comprise a first set of attachment points connected via a first set of the one or more elastic elements so as to form a first digitated pattern, and a second set of attachment points connected via a second set of the one or more elastic elements so as to form a second digitated pattern, and wherein the first and second patterns are arranged in an interdigitated pattern; and (ii) the detector unit is further configured to detect expansion of the expandable member by detecting a change in capacitance due to a change in interdigitation of the first and second patterns.

12. The sensing device of claim 1, wherein the attachment points are connected via elastic elements so as to form a meandering pattern, the attachment points positioned at each turn of the meandering pattern.

13. The sensing device of claim 1, further comprising a sensor element on the one or more elastic elements, the sensor element configured to provide a sensor signal to the detector unit, wherein the sensor signal varies in dependence on an amount of stretching of the one or more elastic elements, further wherein:

the detector unit further comprises a light source and light detector;

the sensor element comprises two optical fibres arranged such that stretching of the one or more elastic elements causes a relative displacement between the two optical fibres;

the sensing device is configured such that the relative displacement between the two optical fibres results in a change in the amount of light reaching the light detector, thereby producing a change in an output signal from the light detector; and the detector unit comprises a gyroscope or an accelerometer configured to detect movement.

14. A combined nappy and sensing device comprising:

a nappy; and a sensing device comprising:

an expandable member comprising one or more elastic elements extending between a plurality of attachment points, wherein the attachment points are configured to fixedly attach the expandable member to an external surface of the nappy, and wherein the one or more elastic elements are configured to stretch as the attachment points move apart such that the expandable member is configured to expand in accordance with expansion of the nappy;

a detector unit coupled to the expandable member, wherein the detector unit is configured to detect expansion of the expandable member, and is further configured to determine a nappy fullness parameter based on the detected expansion of the expandable member; and an electronic control and power supply unit configured to power the sensing device; and wherein the attachment points of the expandable member are fixedly attached to the external surface of the nappy.

15. The combined nappy and sensing device of claim 14, wherein the electronic control and power supply unit comprises the detector unit and the detector unit is mounted on a waistband of the nappy.

16. The combined nappy and sensing device of claim 14, wherein the attachment points of the expandable member are fixedly attached to one of: a front of the nappy, a back of the nappy, a crotch region of the nappy, elasticated edges of the nappy, a waistband of the nappy, or a combination thereof.

17. The combined nappy and sensing device of claim 14, further comprising one or more additional sensing devices, wherein the sensing device and the one or more additional sensing devices are configured to detect expansion at different locations on the external surface of the nappy.

18. The combined nappy and sensing device of claim 14, wherein the electronic control and power supply unit is further configured to calculate at least one of:

a volume of urine and/or feces inside the nappy;

a flow rate of urine inside the nappy; and a frequency of urine and/or feces discharge inside the nappy, wherein the electronic control and power supply unit is configured to calculate at least one of the volume, flow rate, or frequency using one or more software algorithms stored on the device, wherein the one or more software algorithms are based on previously collected empirical data.

19. The combined nappy and sensing device of claim 18, wherein the electronic control and power supply unit is further configured to display at least one of the calculated volume, flow rate, or frequency.

20. The combined nappy and sensing device of claim 18, wherein the electronic control and power supply unit further comprises a wireless transmitter and is further configured to:

store at least one of the calculated volume, flow rate, or frequency; and wirelessly transmit at least one of the calculated volume, flow rate, or frequency to a remote device; and further wherein the expandable member of the sensing device is integrated onto the external surface of the nappy.

\* \* \* \* \*